(12) United States Patent
Miller et al.

(10) Patent No.: US 8,217,344 B2
(45) Date of Patent: Jul. 10, 2012

(54) DIFFERENTIAL MOBILITY SPECTROMETER PRE-FILTER ASSEMBLY FOR A MASS SPECTROMETER

(75) Inventors: Raanan A. Miller, Chestnut Hill, MA (US); Erkinjon G. Nazarov, Lexington, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 804 days.

(21) Appl. No.: 12/012,053

(22) Filed: Jan. 31, 2008

(65) Prior Publication Data

US 2010/0282961 A1    Nov. 11, 2010

Related U.S. Application Data

(60) Provisional application No. 60/899,049, filed on Feb. 1, 2007.

(51) Int. Cl.
*H01J 49/26* (2006.01)
(52) U.S. Cl. .................... 250/290; 250/281; 250/292
(58) Field of Classification Search .............. 250/281, 250/282, 290, 291, 292, 293
See application file for complete search history.

(56) References Cited

U.S. PATENT DOCUMENTS

| | | | |
|---|---|---|---|
| 2,615,135 A | 10/1952 | Glenn | |
| 2,818,507 A | 12/1957 | Britten | |
| 2,919,348 A | 12/1959 | Bierman | |
| 3,511,986 A | 5/1970 | Llewellyn | |
| 3,619,605 A | 11/1971 | Cook et al. | |
| 3,621,240 A | 11/1971 | Cohen et al. | |
| 3,648,046 A | 3/1972 | Denison et al. | |
| 3,931,589 A | 1/1976 | Aisenberg et al. | |
| 4,019,989 A | 4/1977 | Hazewindus et al. | |
| 4,025,818 A | 5/1977 | Giguere et al. | |
| 4,136,280 A | 1/1979 | Hunt et al. | |
| 4,163,151 A | 7/1979 | Bayless et al. | |
| 4,167,668 A | 9/1979 | Mourier | |
| 4,201,921 A | 5/1980 | McCorkle | |
| 4,315,153 A | 2/1982 | Vahrenkamp | |
| 4,517,462 A | 5/1985 | Boyer et al. | |
| 4,761,545 A | 8/1988 | Marshall et al. | |
| 4,885,500 A | 12/1989 | Hansen et al. | |
| 4,931,640 A | 6/1990 | Marshall et al. | |
| RE33,344 E | 9/1990 | Stafford | |
| 5,019,706 A | 5/1991 | Allemann et al. | |
| 5,047,723 A | 9/1991 | Puumalainen | |
| 5,144,127 A | 9/1992 | Williams et al. | |

(Continued)

FOREIGN PATENT DOCUMENTS

CA    2339552    2/2000
(Continued)

OTHER PUBLICATIONS

"A Micromachined Field Driven Radio Frequencey-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05, May 1999.

(Continued)

*Primary Examiner* — David A Vanore
*Assistant Examiner* — Nicole Ippolito

(57) ABSTRACT

A pre-filter assembly including a differential mobility spectrometer (DMS) that is configured to be in-line with a mass spectrometer (MS) such that the MS continuously receives carrier flow from the DMS when the DMS filtering fields are removed.

23 Claims, 36 Drawing Sheets

U.S. PATENT DOCUMENTS

| | | | |
|---|---|---|---|
| 5,218,203 A | 6/1993 | Eisele et al. | |
| 5,298,745 A | 3/1994 | Kernan et al. | |
| 5,373,157 A | 12/1994 | Hiroki et al. | |
| 5,420,424 A | 5/1995 | Carnahan et al. | |
| 5,455,417 A | 10/1995 | Sacristan | |
| 5,492,867 A | 2/1996 | Kotvas et al. | |
| 5,536,939 A | 7/1996 | Freidhoff et al. | |
| 5,541,408 A | 7/1996 | Sittler | |
| 5,644,131 A | 7/1997 | Hansen | |
| 5,654,544 A | 8/1997 | Dresch | |
| 5,723,861 A | 3/1998 | Carnahan et al. | |
| 5,736,739 A | 4/1998 | Uber et al. | |
| 5,763,876 A | 6/1998 | Pertinarides et al. | |
| 5,789,745 A | 8/1998 | Martin et al. | |
| 5,801,379 A | 9/1998 | Kouznetsov | |
| 5,811,059 A | 9/1998 | Genovese et al. | |
| 5,834,771 A | 11/1998 | Yoon et al. | |
| 5,838,003 A | 11/1998 | Bertsch et al. | |
| 5,852,302 A | 12/1998 | Hiraishi et al. | |
| 5,869,344 A | 2/1999 | Linforth et al. | |
| 5,965,882 A | 10/1999 | Megerle et al. | |
| 6,049,052 A | 4/2000 | Chutjian et al. | |
| 6,051,832 A | 4/2000 | Bradshaw | |
| 6,066,848 A | 5/2000 | Kassel et al. | |
| 6,107,628 A | 8/2000 | Smith et al. | |
| 6,124,592 A | 9/2000 | Spangler | |
| 6,157,029 A | 12/2000 | Chutjian et al. | |
| 6,157,031 A | 12/2000 | Prestage | |
| 6,188,067 B1 | 2/2001 | Chutjian et al. | |
| 6,200,539 B1 | 3/2001 | Sherman et al. | |
| 6,262,416 B1 | 7/2001 | Chutjian et al. | |
| 6,281,494 B1 | 8/2001 | Chutjian et al. | |
| 6,323,482 B1 | 11/2001 | Clemmer et al. | |
| 6,495,823 B1 | 12/2002 | Miller et al. | |
| 6,504,149 B2 | 1/2003 | Guevremont et al. | |
| 6,509,562 B1 | 1/2003 | Yang et al. | |
| 6,549,079 B1 | 4/2003 | Crook | |
| 6,618,712 B1 | 9/2003 | Parker et al. | |
| 6,639,212 B1 | 10/2003 | Guevremont et al. | |
| 6,653,627 B2 | 11/2003 | Guevremont et al. | |
| 6,690,004 B2 | 2/2004 | Miller et al. | |
| 6,703,609 B2 | 3/2004 | Guevremont et al. | |
| 6,713,758 B2 | 3/2004 | Guevremont et al. | |
| 6,753,522 B2 | 6/2004 | Guevremont et al. | |
| 6,770,875 B1 | 8/2004 | Guevremont et al. | |
| 6,774,360 B2 | 8/2004 | Guevremont et al. | |
| 6,787,765 B2 | 9/2004 | Guevremont et al. | |
| 6,799,355 B2 | 10/2004 | Guevremont et al. | |
| 6,806,466 B2 | 10/2004 | Guevremont et al. | |
| 6,822,224 B2 | 11/2004 | Guevremont | |
| 6,825,461 B2 | 11/2004 | Guevremont et al. | |
| 6,972,407 B2 | 12/2005 | Miller et al. | |
| 7,550,717 B1* | 6/2009 | Belford et al. | 250/281 |
| 2001/0030285 A1 | 10/2001 | Miller et al. | |
| 2002/0070338 A1 | 6/2002 | Loboda | |
| 2002/0134932 A1 | 9/2002 | Guevremont et al. | |
| 2003/0020012 A1 | 1/2003 | Guevremont | |
| 2003/0038235 A1* | 2/2003 | Guevremont et al. | 250/287 |
| 2003/0052263 A1 | 3/2003 | Kaufman et al. | |
| 2003/0089847 A1 | 5/2003 | Guevremont et al. | |
| 2003/0132380 A1 | 7/2003 | Miller et al. | |
| 2003/0146377 A1* | 8/2003 | Miller et al. | 250/286 |
| 2004/0094704 A1 | 5/2004 | Miller et al. | |
| 2004/0232326 A1 | 11/2004 | Guevremont et al. | |
| 2005/0023457 A1* | 2/2005 | Miller et al. | 250/288 |
| 2005/0145789 A1* | 7/2005 | Miller et al. | 250/290 |
| 2007/0272852 A1 | 11/2007 | Miller et al. | |

FOREIGN PATENT DOCUMENTS

| | | |
|---|---|---|
| WO | WO-9619822 | 6/1996 |
| WO | WO-9738302 | 10/1997 |
| WO | WO-9908309 | 2/1999 |
| WO | WO-9921212 | 4/1999 |
| WO | WO-0008454 | 2/2000 |
| WO | WO-0008455 | 2/2000 |
| WO | WO-0008456 | 2/2000 |
| WO | WO-0008457 | 2/2000 |
| WO | WO-0048228 | 8/2000 |
| WO | WO-0108197 | 2/2001 |
| WO | WO-0122049 | 3/2001 |
| WO | WO-0135441 | 5/2001 |
| WO | WO-0169217 | 9/2001 |
| WO | WO-0169220 | 9/2001 |
| WO | WO-0169647 | 9/2001 |
| WO | WO-02071053 | 9/2002 |
| WO | WO-02083276 | 10/2002 |

OTHER PUBLICATIONS

"Advanced Cross-Enterprise Technology Development for NASA Missions," Revised NASA Research Annoucement NRA99-OSS-05, pp. 1-C19 (1999).

Krylov, "Comparison of the Planar and Coaxial Field Asymmetrical Waveform Ion Mobility Spectrometer (FAIMS)," International Journal of Mass Spectrometry, 225, pp. 39-51 (2003).

Barnett, et al., "Isotope Separation using High-Field Asymmetric Waveform Ion Mobility Spectrometry," Nuclear Instruments & Methods in Physics Research, vol. 450, No. 1, pp. 179-185 (2000).

Buryakov et al., "A New Method of Separation of Multi-Atomic Ions by Mobility at Atmospheric Pressure Using a High-Frequency Amplitude-Asymmetric Strong Electric Field," International Journal of Mass Spectrometry and Ion Processes, vol. 128, pp. 143-148 (1993).

Buryakov et al., "Device and Method for Gas Electrophoresis, Chemical Analysis of Environment," edit Prof. V.V. Malakhov, Novosibirsk: Nauka pp. 113-127 (1991).

Buryakov et al., "Drift Spectrometer for the Control of Amine Traces in the Atmosphere," J. Anal. Chem., vol. 48, No. 1, pp. 112-121 (1993).

Buryakov et al., "Separation of Ions According to Mobility in a Strong AC Electric Field," Letters to Journal of Technical Physics, vol. 17, pp. 11-12 (1991).

Carnahan et al, "Field Ion Spectrometry—A New Technology for Cocaine and Heroin Detection," SPIE, 2937:106-119 (1997).

Carnahan, et al., "Field Ion Spectrometry—A New Analytical Technology for Trace Gas Analysis," ISA, vol. 51, No. 1, pp. 87-96 (1996).

Guevrement, R. et al., "Atmospheric Pressure Ion Focusing in a High-Field Asymmetric Waveform Ion Mobility Spectrometer," Review of Scientific Instruments, vol. 70, No. 2, pp. 1370-1383 (1999).

Guevremont et al., "Calculation of Ion Mobilities from Electrospray Ionization High Field Asymmetric Waveform Ion Mobility Spectrometry Mass Spectrometry," Journal of Chemical Physics, 114(23):10270-10277 (2001).

Guevremont, et al., "High Field Asymmetric Waveform Ion Mobility Spectrometry-Mass Spectrometry: An Investigation of Leucine Enkephalin Ions Produced by Electrospray Ionization," J. Am. Soc. Mass. Spectrom., vol. 10, pp. 492-501 (1999).

Handy et al., "Determination of Nanomolar Levels of Perchlorate in Water by ESI-FAIMS-MS," J. Anal. At. Spectrometry, vol. 15, pp. 907-911 (2000).

Javahery, et al., "A Segmented Radio Frequency-Only Quadrupole Collision Cell for MEasurements of Ion Collision Cross Section on a Triple Quadrupole Mass Spectrometer," J. Am. Soc. Mass. Spectrom., vol. 8, pp. 697-702 (1997).

Krylov, "A Method of Reducing Diffusion Losses in a Drift Spectrometer," Technical Physics, 44(1):113-116 (1999).

Krylov, "Pulses of Special Shapes Formed on a Capacitive Load," Instruments and Experimental Techniques, vol. 40, No. 5 (1997???). International Academic Publishing Company (IAPC), Russia, E. Krylov.

Miller et al., "A Novel Micromachined High-Field Asymmetric Waveform-Ion Mobility Spectrometer," Sensors and Actuators B, vol. B67, No. 3, pp. 300-306 (2000).

Pilzecker et al., "On-Site Investigations of Gas Insulated Substations Using Ion Mobility Spectrometry for Remote Sensing of SF6 Decomposition," IEEE, pp. 400-403 (2000).

Raizer, Y.P., et al., Radio-Frequency Capacitive Discharges, CRC Press, pp. 1-3 (1995).

Riegner et al., "Qualitative Evaluation of Field Ion Spectrometry for Chemical Warfare Agent Detection," Proceedings of the ASMS Conference on Mass Spectrometry and Allied Topics, pp. 473A-473B (1997).

Verenchikov et al, "Analysis of Ionic Composition of Solutions using an Ion Gas Analyzer," Chemical Analysis of Environment, edit. Prof. V.V. Malakhov, Novosibirsk, Nauka, pp. 127-134 (1991).

International Search Report and Written Opinion dated May 8, 2009 in International Application No. PCT/US2008/001415.

* cited by examiner

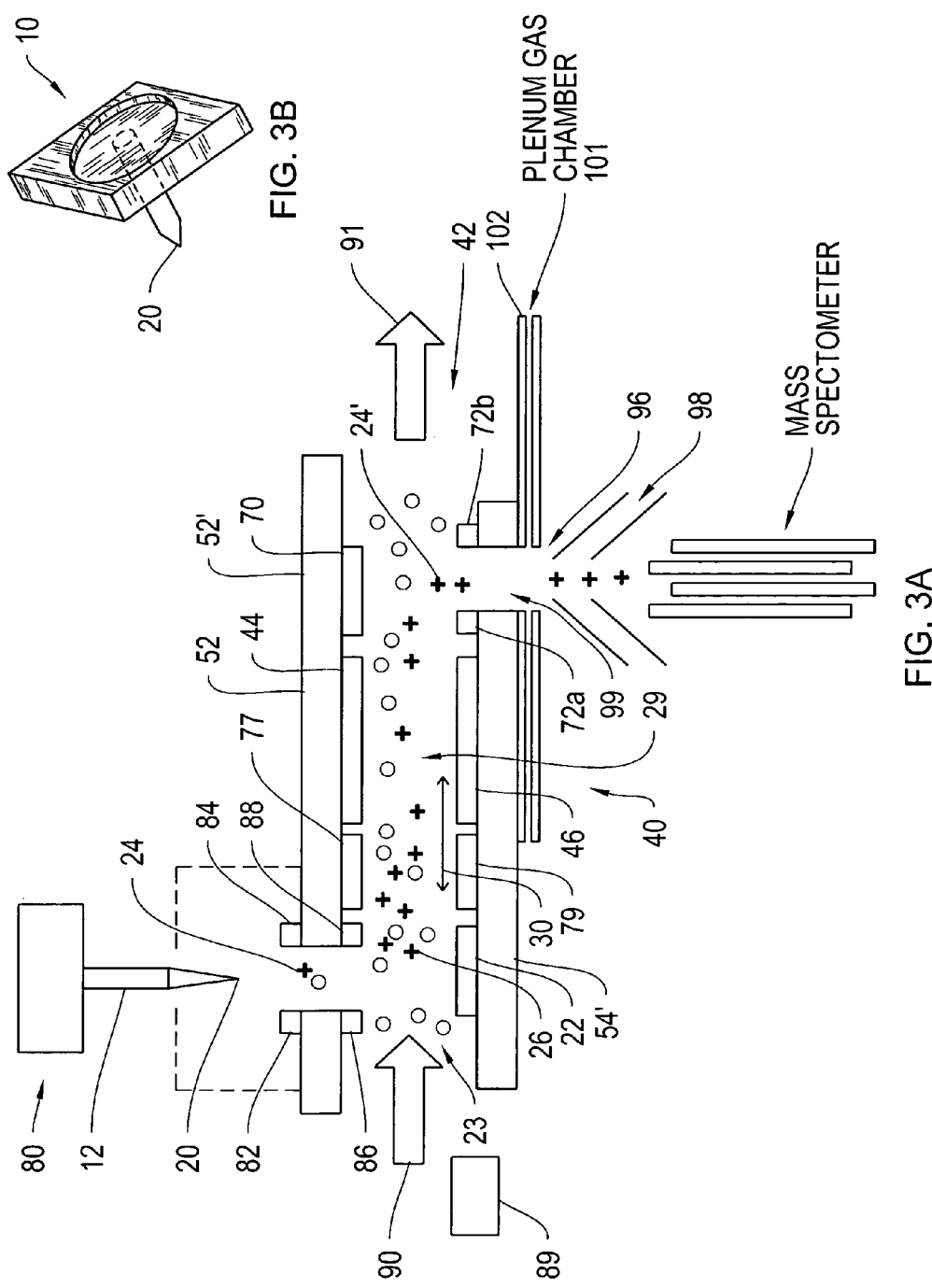

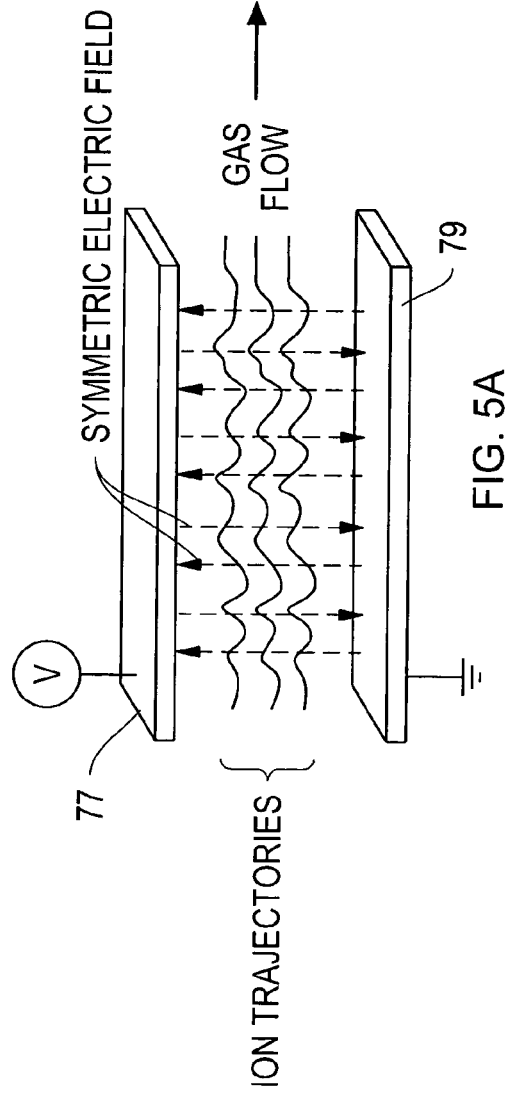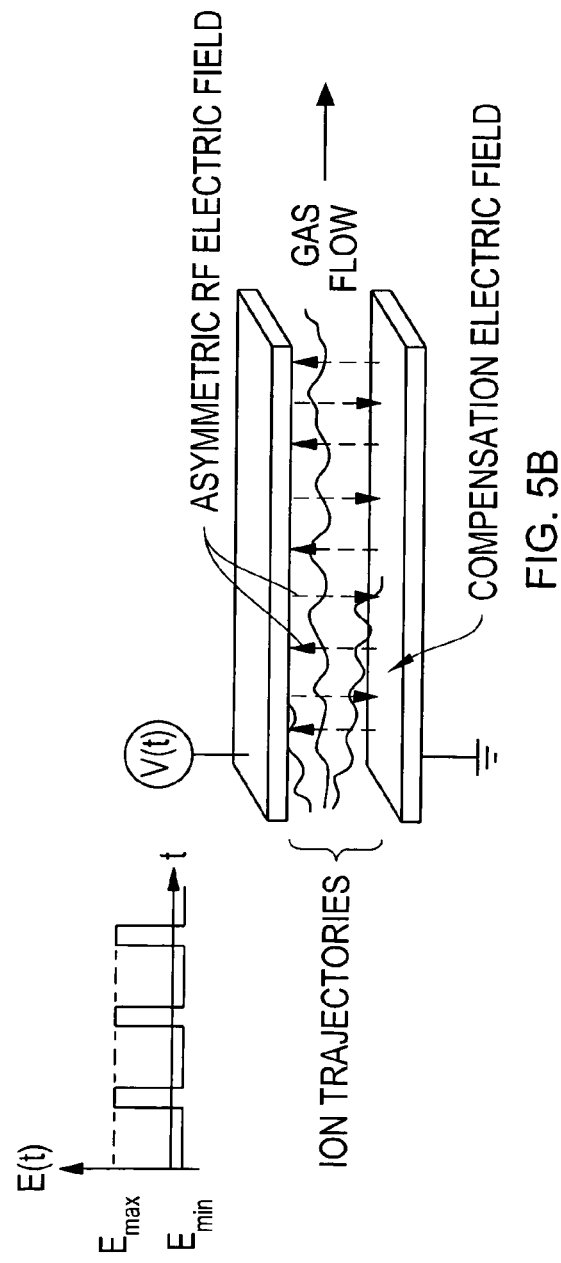

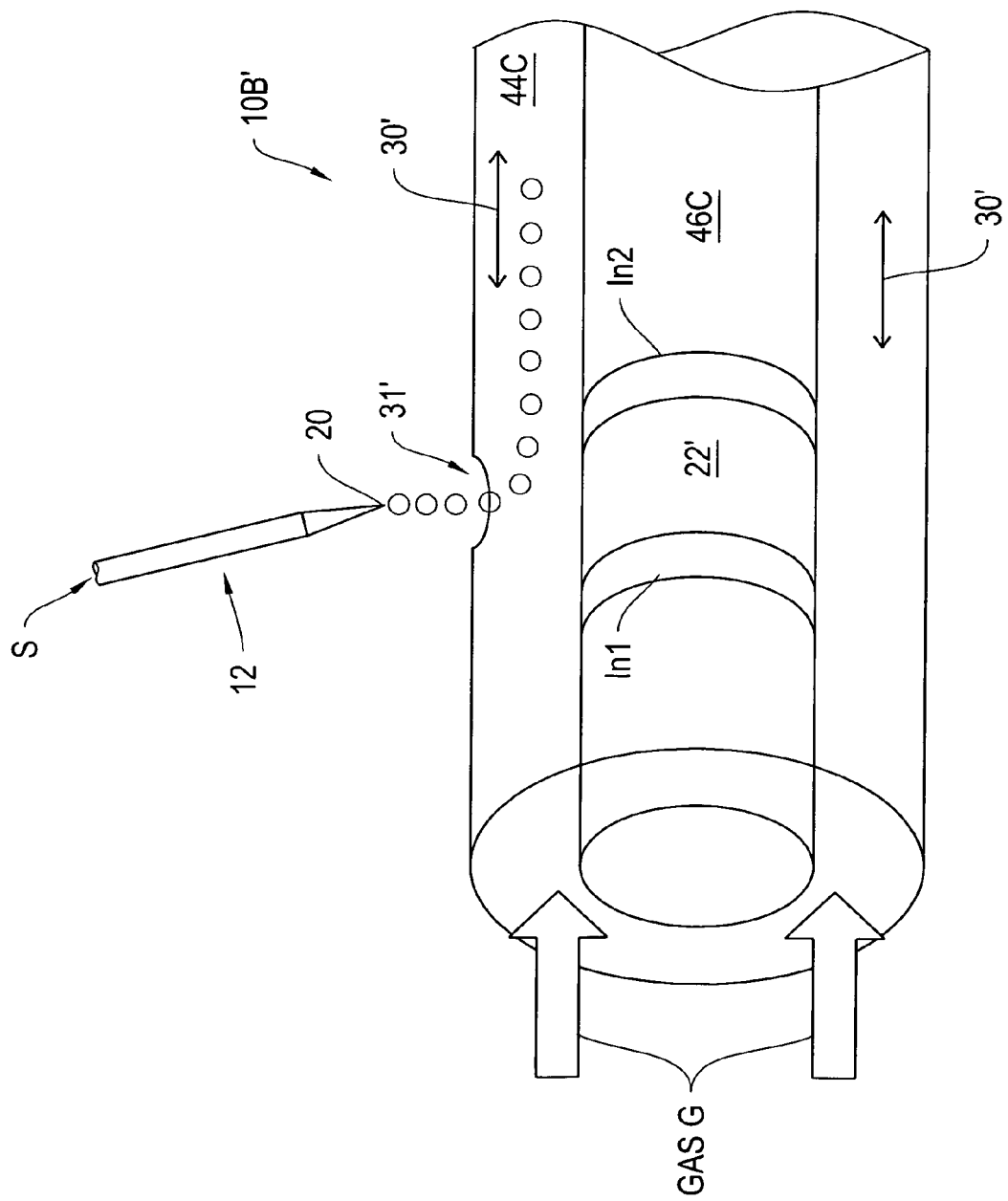

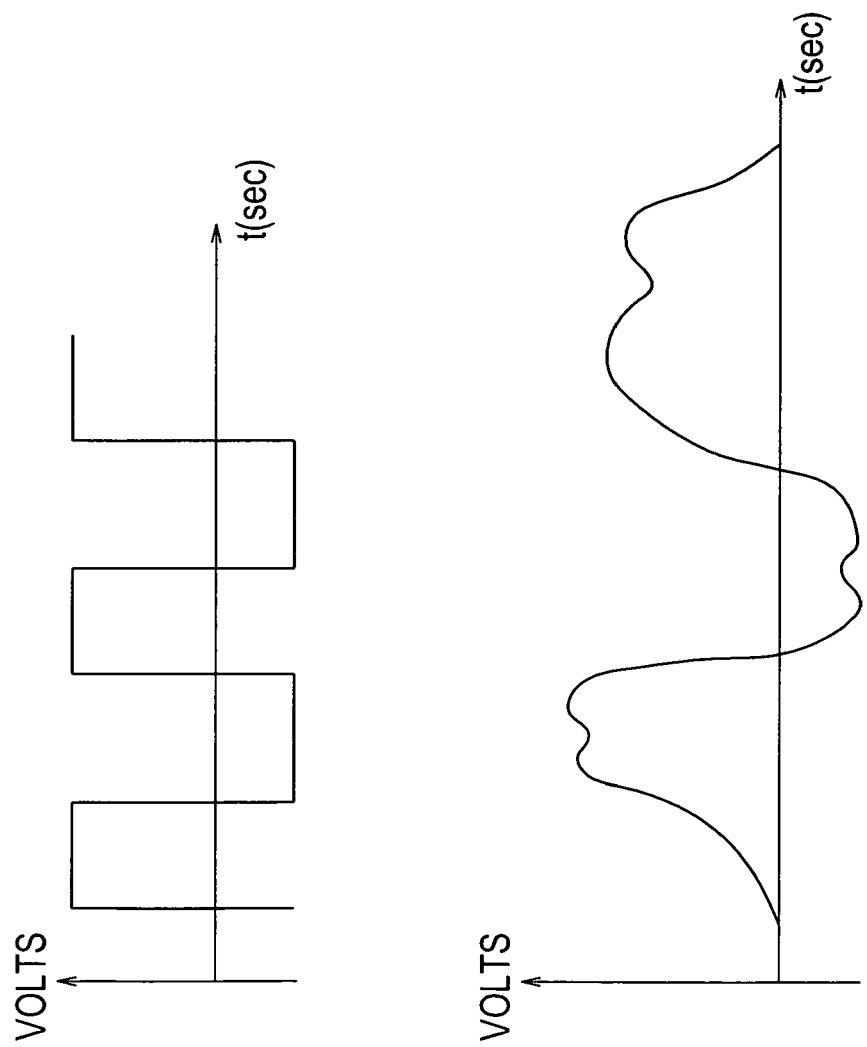

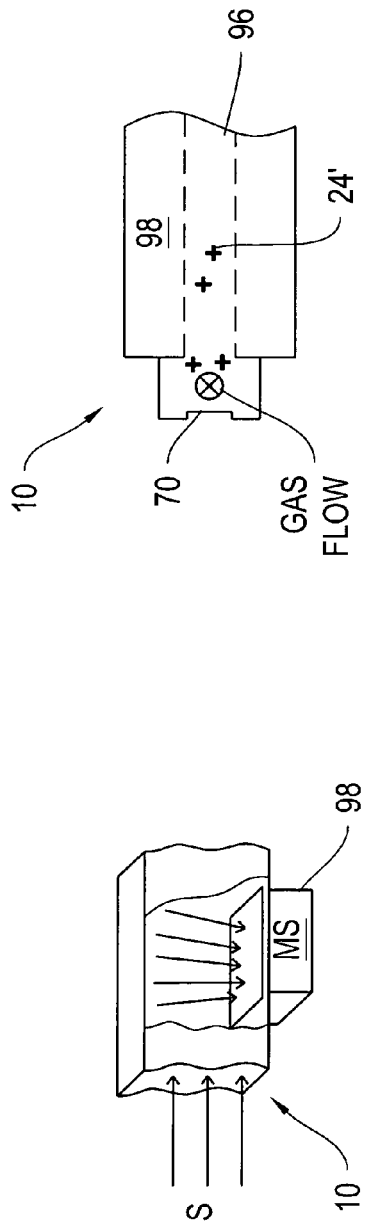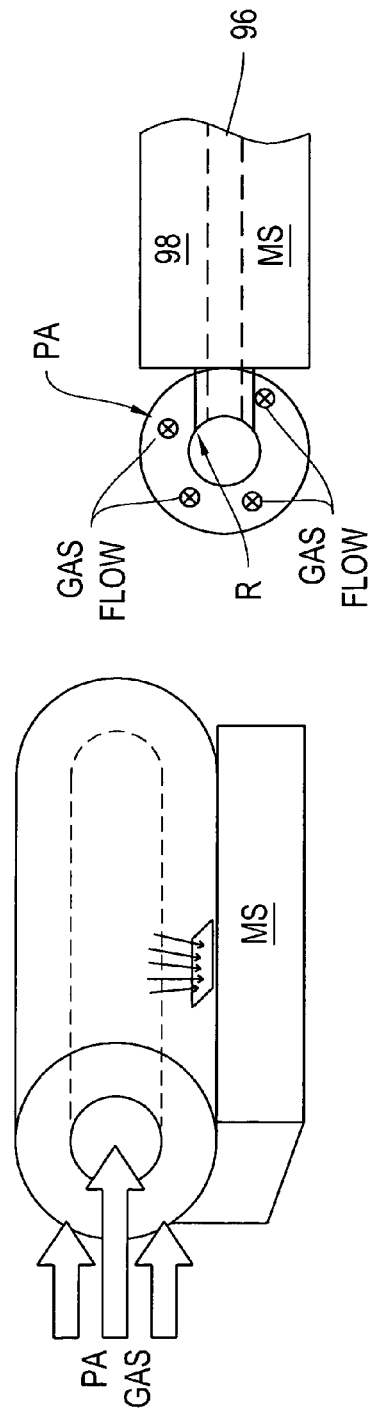
FIG. 12A
FIG. 12B
FIG. 12C (PRIOR ART)
FIG. 12D (PRIOR ART)

DIFFERENTIAL MOBILITY SPECTROMETER PRE-FILTER ASSEMBLY FOR A MASS SPECTROMETER

REFERENCE TO RELATED APPLICATIONS

This application claims priority to and the benefit of U.S. Provisional Application No. 60/899,049, filed on Feb. 1, 2007, the entire contents of which are incorporated herein by reference.

FIELD OF THE INVENTION

This invention relates to ion mobility based spectrometers such as ion mobility spectrometers and differential mobility spectrometers, and more particularly, to differential mobility spectrometers operating as pre-filters for mass spectrometers.

BACKGROUND

Ion mobility based analyzers, such as ion mobility spectrometers and differential mobility spectrometers, analyze ions based on the ions' mobility characteristics while the ions are flowing through a gas or mixture of gases. An ion mobility spectrometer (IMS) typically uses a voltage gradient to propel ions along a drift region toward a detector. A time-of-flight (TOF) IMS separates and discriminates among different ion species by measuring the arrival time of the different ions species at a detector because ions species having different ion mobility characteristics travel through a drift gas at different rates.

A differential mobility spectrometer (DMS), also referred to as a Field Asymmetric Ion Mobility Spectrometer (FAIMS), also analyzes ions that are flowing through a gas or mixture of gases. However, unlike an IMS, a DMS subjects the ions to a time-varying (e.g., asymmetric) field as the ions flow through an analytical gap between filter electrodes that apply the asymmetric field. The asymmetric field typically includes a high field period followed by longer low field period. A compensation field is also typically generated one of the filter electrodes (by applying a DC compensation voltage to the electrode) that enables the DMS to pass through a selected ion species. Other species are typically deflected toward one of the filter electrodes and neutralized. Ion mobility based analyzers, such as an IMS or DMS, are capable of identifying samples and sample constituents by measuring an ion intensity spectrum and comparing that spectrum with a known spectrum or spectra.

DMS or DMS analyzers typically have a cylindrical or planar form factor. Cylindrical DMS analyzers, such as those described in U.S. Pat. No. 6,621,077, employ a terminus and trap region to enable the collection and concentration of ions before introduction of the ions from the DMS or DMS into an MS. One problem with this structure is that ions tend to be distributed or diffused by the cylindrical DMS filter which results in the need for a terminus and ion trap to concentrate the ions before introduction into an MS.

Mass analyzers or Mass Spectrometers (MS), unlike ion mobility based spectrometers, measure the mass-to-charge ratio (m/z) of ions by subjecting ions within a vacuum to an accelerating electric field. In a TOF MS, ions having different mass-to-charges ratios are subjected to the same electric field. Because different ion species have different mass-to-charge ratios, the different ion species undergoes different amounts of acceleration and, therefore, arrive at a detector at different times. Hence, a TOF MS is capable of detecting and measuring different ions based on their different mass-to-charge ratios. A MS can identify the components of a sample by determining their molecular weight or mass.

Chip-based or micromachined IMS, DMS, and MS systems are commercially available today. Such micromachined systems are desirable because they enable the use of compact and portable ion detection systems.

IMS, DMS, and MS analyzers often operate as stand-alone systems. However, certain types of combined analyzers such as a tandem IMS-MS, tandem DMS-MS, or tandem IMS-DMS-MS system may be employed. For example, Thermo Fisher Scientific, Inc., of Waltham, Mass., markets a cylindrical DMS (FAIMS) interface that can be interfaced with their TSQ Quantum® series mass spectrometers for laboratory research.

One problem with using a cylindrical DMS or DMS as a pre-filter to a MS is that researchers must attach the cylindrical DMS per-filter to the MS when pre-filtering is desired, but then disconnect and remove the cylindrical DMS pre-filter from the MS when analysis without DMS pre-filtering is desired. This is necessary because, as stated above, the cylindrical DMS structure tends to diffuse ions. Thus, if the cylindrical DMS filter is only de-activated without removal, the ions within a cylindrical DMS will no longer be concentrated or trapped prior to entry into the MS, resulting in degraded system sensitivity and performance. Thus, the cylindrical DMS must be disconnected from the MS to prevent the ion diffusion effects of a deactivated cylindrical DMS before ion introduction into the MS. The attachment and detachment requirement of the cylindrical DMS is undesirable for numerous reasons: 1) attachment and detachment may expose the user to sample contamination, 2) attachment and detachment is time-consuming, 3) attachment and detachment requires user training, 4) attachment and detachment may result in excessive wear and failure of the DMS-to-MS connection, 5) attachment and detachment may reduce the reliability of the system, and 6) the detachable DMS interface may be lost or damaged when separated from the MS. Accordingly, there is a need for a DMS or DMS pre-filter to an MS that can be deactivated instead of disconnected when MS analysis without DMS pre-filtering is desired.

Another problem associated DMS-MS analyzers is that the relatively high transport gas flow rate of a DMS can result in a relatively high flow rate into the attached MS. Because an MS must maintain a high vacuum, a relatively powerful and, therefore, large pump is required to maintain such a high vacuum at the relatively high ion flow rate. While the size of a DMS-MS system may not be a concern in a laboratory environment, DMS-MS system size and power requirements are critical for portable, field-deployable, or in-situ sample analysis applications and uses. Accordingly, there is a need to reduce the size of the vacuum pump used for the MS to realize a more compact, portable, and less power-consuming DMS-MS system.

SUMMARY

The invention, in various embodiments, addresses deficiencies in the prior art by providing systems, methods and devices that enable a DMS to be coupled to a MS in such ways as to enhance the safety and efficiency DMS-MS experimental operations and to enhance the portability and compactness of DMS-MS analyzers.

In one aspect, the invention includes system for analyzing one or more ion species of a sample. The system includes an ion source for forming sample constituents into ions. The system also includes a pre-filter assembly. The assembly may further include a DMS filter that passes one or more ion species of the sample through a time-varying field in an analytical gap between a pair of filter electrodes. The assembly may also include an outlet that provides a flow of ions from the DMS filter to an MS. The MS may receive, at an inlet, at least a portion of the flow of ions from the pre-filter assembly and analyze one or more ion species. The system may include a controller that activates the DMS filter when pre-filtering is desired and deactivating the DMS filter when pre-filtering is not desired. Preferably, the DMS filter is positioned substantially in-line with the inlet of the mass spectrometer.

In one configuration, the DMS filter is in-line with the inlet of the mass spectrometer when the longitudinal axis of the analytical gap between the pair of filter electrodes is aligned with the longitudinal axis of the inlet of the first mass spectrometer. The time-varying field may be adjustable and include an adjustable compensation field.

In another configuration, the controller includes a microprocessor. The ion source may include an electrospray ion source. In certain configurations, a liquid chromatograph (LC) may be coupled to the system to enable the delivery of a liquid sample to the electrospray ion source. The process of analyzing may include the detection one or more ion species.

In a further configuration, the system may include a second mass spectrometer that receives and detects ions from a first mass spectrometer. In this instance, the analyzing by the first mass spectrometer may include focusing a portion of the ions received from the DMS. The DMS may include one or more insulating substrates where at least one insulting substrate is in communication with a filter electrode. The DMS, MS and/or any other components of the system may be included in a chip assembly.

In another aspect, the size and power consumption of a DMS-MS analyzer system are reduced by orienting the MS in relation to the DMS in such a way as to enable a significantly lower ion flow rate into the MS. Thus, a significantly smaller vacuum pump or pumps are required to maintain the proper vacuum in the MS which, thereby, reduces the DMS-MS analyzer size and power requirements.

The DMS-MS analyzer or ion analyzer may include a flow generator that generates a flow of ions from an ion source at a first flow rate. The flow generator may include a pump, micromachined pump, pressure source, solid-state flow generator, and other like flow generator. The ion analyzer may include a chip assembly that is coupled to receive the flow of ions from the ion source. The chip assembly may include a spaced filter having a first substrate with a first filter electrode connected to the substrate. The assembly may include a second filter electrode that is spaced away from the first filter electrode to, thereby, define an analytical gap between the first and second filter electrodes and a portion of a flow path through which the ion flow occurs.

The assembly may include a mass spectrometer that receiving a portion of the ions from the flow path. The mass spectrometer may includes an inlet that is offset from the flow of ions in the flow path. Because the inlet is offset, the chip assembly may include a diverter assembly for flowing a portion of the ions from the flow path into the inlet of the mass spectrometer. The portion of ions from the first flow path may be flowed through the inlet at a second flow rate where the second flow rate is less than the first flow rate.

The analyzer may include a controller that is connected to at least one of the first and second filter electrodes to generate a time varying electric field between the first and second filter electrodes. The time-varying field may include a field characteristic for separating ion species while the ion species are flowing through the analytical gap. The analyzer may include a vacuum generator for maintaining a selected vacuum within the mass spectrometer in response to the second flow rate at the inlet of the mass spectrometer. The vacuum generator may include one or more pumps, micromachined pumps, pressure sources, solid-state flow generators, and the like.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3A shows a chemical sensor system with liquid sample preparation section including an electrospray source according to an illustrative embodiment of the invention.

FIG. 3B shows a machined electrospray head according to an illustrative embodiment of the invention.

FIG. 5A shows symmetric AC radio frequency field for ion desolvation according to an illustrative embodiment of the invention.

FIG. 5B shows the desolvation region integrated into a DMS device according to an illustrative embodiment of the invention.

FIGS. 7A and 7B show an enhanced cylindrical DMS device according to an illustrative embodiment of the invention.

FIG. 10B shows control signals according to an illustrative embodiment of the invention.

FIGS. 12A and 12B show planar DMS analyzers according to an illustrative embodiment of the invention.

FIGS. 12C and 12D show prior art cylindrical DMS devices.

ILLUSTRATIVE DESCRIPTION

Figure 1:
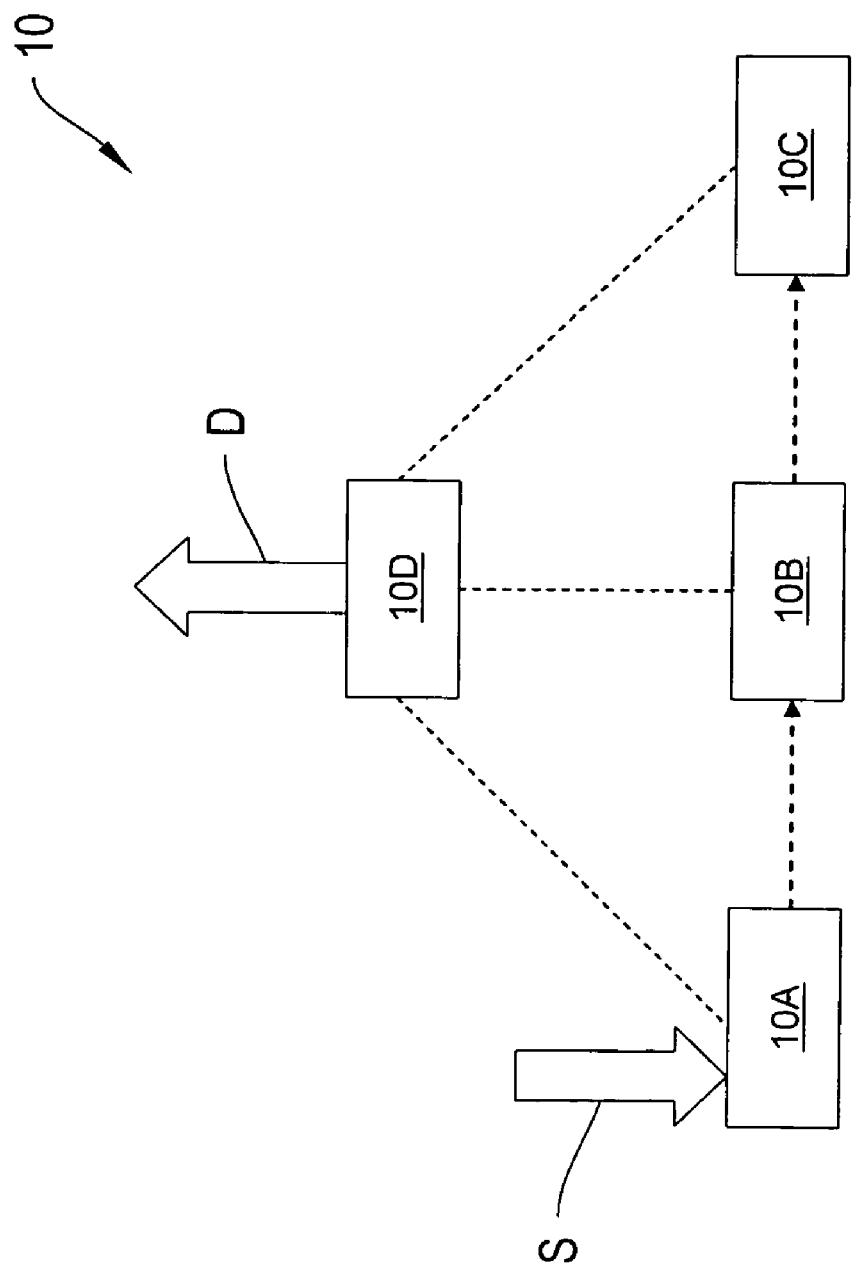
FIG. 1 shows a block diagram of a chemical sensor system according to an illustrative embodiment of the invention.

A description of preferred embodiments of the invention follows. The present invention provides method and apparatus for analysis of compounds using a DMS pre-filter for a mass spectrometer.

Electrospray mass spectrometry (ES-MS) provides a powerful tool for structure determination of peptides and/or proteins. This is important because the structure helps define the function of the protein. The structural information about a protein is typically determined from its amino acid sequence. To identify the sequence, the protein is usually digested by enzymes and the peptide fragments are then sequenced by tandem mass spectrometry. Another possible way to obtain the sequence is to digest the protein and measure the molecular weights of the peptide fragments. These are the input data for a computer program which digests theoretically all the proteins being found in the data base and the theoretical fragments are compared with the measured molecular weights.

Recently, it has been noticed that ion mobility based analysis such as by IMS can provide useful information to an ES-MS measurement. Ion mobility based analysis is ordinarily an atmospheric pressure technique which is highly sensitive to the shape and size of a molecule. Protein identification thorough the combination of an IMS and MS may eliminate the need for protein digestion, simplifying sample preparation.

Commercially available IMS systems are based on time-of-flight (TOF), i.e., they measure the time it takes ions to travel from a shutter-gate to a detector through an inert atmosphere (1 to 760 Torr). The drift time is dependent on the mobility of the ion (i.e., its size, mass and charge) and is characteristic of the ion species detected. TOF-IMS is a technique useful for the detection of numerous compounds including narcotics, explosives, and chemical warfare agents. See PCT Application Serial No. PCT/CA99/00715 incorporated herein by this reference and U.S. Pat. No. 5,420,424 also incorporated herein by this reference. Gas-phase ion mobility in an IMS is determined using a drift tube with a constant low field strength electric field. Ions are gated into the drift tube and are subsequently separated based on differences in their drift velocity. The ion drift velocity under these conditions is proportional to the electric field strength and the ion mobility. Current IMS devices use conventionally machined drift tubes (minimum size about 40 $cm^3$) for ion identification.

A DMS (also known as a FAIMS or RF-IMS) utilizes significantly higher electric fields, and identifies the ion species based on the difference in its mobility in high and low strength electric fields. A DMS uses an ionization source, such as an ultra violet photo-ionization lamp, to convert a gas sample into a mixture of ion species with each ion type corresponding to a particular chemical in the gas sample. The ion species are then passed through an ion filter where particular electric fields are applied between electrodes to select an ion type allowed to pass through the filter.

Once through the filter, the ion species hits a detector electrode and produces an electrical signal. To detect a mixture of ion species in the sample, the electric fields applied between the filter electrodes can be scanned over a range and a spectrum generated. The ion filtering is achieved through the combination of two electric fields generated between the ion filter electrodes, a time-varying (e.g., asymmetric and periodic) radio frequency (RF) electric field, and a dc compensation electric field. The asymmetric RF field has a significant difference between its peak positive field strength and negative field strength. The asymmetric RF field scatters the ions and causes them to deflect to the ion filter electrodes where they are neutralized, while the compensation field prevents the scattering of a particular ion allowing it to pass through to the detector. The ions are filtered in DMS analyzers on the basis of the difference in the mobility of the ions at high electric fields relative to the ions' mobility at low electric fields.

A DMS ion filter may be employed to filter ions by control of a variable DC compensation signal in addition to a time-varying or high field asymmetric waveform radio frequency signal. A DMS filter may control ion filtering by varying the wavelength, frequency, amplitude, period, duty cycle or the like of the high field asymmetric waveform radio frequency signal. A DMS filter may include planar DMS filter structure using insulating substrates to accurately define the gap between the ion filter electrodes and/or ensure the ion filter electrodes are parallel. The use of a micromachined substrate-based DMS may enable consistent, reliable, and reproducible fields to be generated by the DMS filter, resulting in a higher resolution DMS analyzer.

A DMS filter may be employed with a sample spray source, such as electrospray (ES), where desolvation of the ions is very important in order to obtain reliable, reproducible spectra. Desolvation electrodes may be included to assist in desolvation, where enhanced desolvation is achieved by applying symmetric RF signals to the desolvation electrodes. The RF signals provide energy to the ions which raises their effective temperature and helps to enhance the desolvation process. Desolvation electrodes can also be used to control the level of ion clustering in gas samples from electrospray and from other than electrospray sources. Control of ion clustering can permit more repeatable measurements and also can provide additional information on the ions being detected.

An ES-DMS system may employ an electrospray head and use an attraction electrode which is separated from the ion filter electrodes. Separating the attraction electrode from the ion filter electrodes enables independent control of the potential applied to the attraction electrode relative to the ion filter electrodes. Independent attraction electrode control allows for optimization of the electrospray conditions and ion introduction conditions into the DMS. The separation of attraction electrode from the ion filter electrodes can also be realized in cylindrical DMS configurations.

An ES-DMS may include guiding electrodes that provide further optimization of ion injection into the DMS ion filter. An electrospray assembly can be attached to one of the substrates of the DMS and guiding electrodes may be used to guide the ions into the ionization region. The guiding electrodes may include a freestanding structure attached or connected to or near one of the substrates of the DMS. The assembly may include and/or utilize a counter gas flow to enhance desolvation.

In an ES-DMS system, a time-of-flight (TOF) measurement may be combined with a DMS filter approach using electrospray to enhance identification of the ion species through the additional information provided by the time-of-flight measurement. The time it takes for an ion to travel from the orifice of the DMS to the detector can be measured. This can be achieved through the independent control of the attraction and guiding electrode potentials. Initially the attraction electrode potential can be adjusted so that no ions make it into the drift region, but rather are collected at the guiding electrodes. Then the attraction electrode can be pulsed so that some ions can make it into the ionization region and into the DMS filter. The time it takes for the ions to travel from the ionization region to the detector can be measured, and this provides additional discriminating information on the identity of the ions.

Portions of the ES-DMS system may be micromachined or fabricated using semi-conductor fabrication techniques. Certain DMS electrodes may be formed on an insulating or insulated substrate where the insulating substrate or substrates can form a housing or chip assembly. Micromachining ES-DMS components into chip assemblies and/or multichip modules advantageously results in low cost, miniature sensors.

An ES-DMS system may include an output section with the ability to detect multiple ion species simultaneously such as a positively and negatively charged ion. Because sample analysis in a DMS analyzer is generally performed in the gas phase, liquid samples require conversion from the liquid to the gas phase. Thus, an electrospray (ES) method (which may include "conventional", micro and/or nanospray) may be used to convert a liquid sample into gas phase ions. The ions streaming out of the electrospray tip may be delivered to a planar DMS analyzer. In an ES-DMS system, all the functions of sample preparation, ionization, filtering and detection may be performed on a single "chip".

An ES-DMS system may be combined with a mass spectrometer to form an ES-DMS-MS analyzer. The DMS coupled to the MS enhances the MS detection process by enhancing resolution, establishing better detection limits, enabling the extraction of shape and structure information of the molecules being analyzed, and enabling the improved analysis of molecules such as bio-molecules including proteins and peptides. DMS analysis is based on ion mobility, where ion filtering and identification is highly dependent on the size and shape of the ion which may be valuable for genomics and proteomics research (i.e., pharmaceutical industry) because the shape of a protein to a large extent determines its functionality. Therefore, DMS filtering may be applied as a low cost, but high volume, method of protein characterization.

A disposable DMS filter chip may be employed that is plugged into a carrier mounted on the inlet of a MS. The ES-DMS-MS device may also provide structural (conformation) information about molecules being analyzed and sequence information not obtainable by ES-MS analysis alone. A DMS analyzer may enable discrimination between isomers (molecules with the identical mass but which differ in their shape) which cannot be identified using ES-MS alone.

An ES-DMS analyzer may be included in a single housing. An ES-DMS analyzer may be used as a stand alone sensor for liquid sample analysis or as the front end to a MS. An ES-DMS and/or ES-DMS-MS analyzer may operate with other liquid separation techniques such as liquid chromatography (LC), high pressure liquid chromatography, and capillary electrophoresis. For example, an LC-ES-DMS-MS system may be employed. A portion or all of the LC-ES-DMS-MS system may be micromachined and/or formed on a chip assembly. The DMS filter portion may include a planar DMS, a cylindrical DMS and/or coaxial DMS.

Micromachining (MEMS) processing can enable the integration of an electrospray tip with a DMS filter into a simple device and results in a precise yet compact analytical system for accurate, highly repeatable, liquid sample evaluation. The MEMS ES-MS may be used as a portable, miniature, low cost, bio-sensor for biological agent detection. An integrated ES-DMS chip may be prepared using micromachining fabrication techniques. An atmospheric pressure chemical ionization (APCI) device may be integrated with a DMS filter used as a prefilter to a mass spectrometer to form an integrated APCI-DMS-MS analyzer.

Conventional machining has typically involved high cost fabrication and poor reproducibility of DMS analyzers. For instance, the cylindrical DMS geometry either limits collection efficiency when interfacing to a MS, or permits both sample neutrals and sample ions to enter the MS, resulting in more complex spectra. In a planar and/or micromachined DMS, formation of the DMS is more precise and consistent, resulting in significantly more reliable mass spectra for the identification of the bio-molecules.

A micromachined ES-DMS is a low cost, a volume manufacturable, small and compact, spectrometer based on differential ion mobility. Thus, ES-DMS systems may be produced using high volume manufacturing techniques, such as MEMS fabrication techniques which includes ceramic packaging, PC board manufacturing techniques or plastic processing. The volume manufacture techniques can result in low cost devices that can be made disposable, thus avoiding the problem of sample cross contamination. ES-DMS chips may be provided to any laboratory using a MS for biological molecule identification as a DMS interface filter. Such a filter may include a DMS interface chip which can plug into an interface fixture which contains filtering electronics. The electrospray tip or electrophoresis chips can be integrated with (fabricated as part of) the DMS chip. The MEMS approach is not required but may be preferred because the approach 1) enables high reliability and repeatability in volume manufactured DMS chips and 2) lowers DMS cost and enables disposable DMS analyzers. This disposability avoids contamination from one sample to the next (or to a user), which is invaluable for tests performed subject to, for and/or by regulatory agencies like the EPA and FDA where contamination is a concern.

A planar MEMS DMS chip was fabricated in which ions are focused into a mass spectrometer and collection efficiency is close to 100%. In this embodiment, no ion injection is required into the DMS ion filter region. The device is micromachined on a planar surface. This enables easy integration with onboard heaters to minimize ion clustering. It can be easily integrated with micromachined or conventional electrospray tips and/or micromachined electrophoresis chips. This is a simplified design with reduced fabrication requirements, and can be configured to use only a single gas flow channel.

Micromachining provides for excellent reproducibility in the manufacture and performance of the filters. This is critical so that test results are consistent from one device to the next and from one laboratory to the next. Micromachining enables new configurations of DMS filter chips which cannot be made any other way. These new configurations are simpler and more efficient at delivering ions to the mass spectrometer and filtering unwanted ions.

Portable, miniature, low cost, bio-sensors for biological agent detection which use an integrated ES-DMS chip are possible using microfabrication methods such as micromachining s because of the size reduction and cost reductions enabled by this technology and enabled manufacture. These instruments may have many uses, including availing high quality bio-analysis in the field. For example, a person suspected of being exposed to a bio-agent can supply a drop of blood to the instrument. The blood can be mixed with a buffer solution, processed, and introduced via the electrospray nozzle into the DMS where the ions are analyzed. If a particular bio-molecule is detected an alarm can be set off.

A MEMS DMS may include a multi-use housing/substrate/packaging that simplifies formation of the component parts and resulting assembly. Additional features may include using the substrate as a physical platform to build the filter upon and to give structure to the whole device, to use the substrate as an insulated platform or enclosure that defines the flow path through the device, and/or use the substrate to provide an isolating structure that improves performance. A spacer can be incorporated into the device, which provides both a defining structure and also the possibility of a pair of silicon electrodes for further biasing control. Multiple electrode formations and a functional spacer arrangement can be utilized which improve performance and capability. A MEMS DMS may employ a time-varying and/or asymmetric periodic voltage applied to its filters. A control component can include a heater for purging ions, and may even include use of the existing electrodes, such as filter or detector electrodes, for heating/temperature control.

An ES-DMS-MS system may include all functions of sample preparation, ionization, filtering and detection can be performed on a single chip, assembly, or structure. A DMS analyzer may be applied as a pre-filter to a MS where the MS is directly coupled to an exhaust port at the end of a DMS filter region. Various sample preparation sections may be used including: a port to draw in ambient air samples, electrospray, gas chromatograph, and/or a liquid chromatograph, or the like.

FIG. 1 shows a block diagram of a chemical sensor system 10 that includes a sample preparation section 10A, a filter section 10B, and an output section 10C. In practice, a liquid sample S is ionized in sample preparation section 10A, the created ions then being passed to and filtered in filter section 10B, and then ions passing through the filter section are delivered to output section 10C for detection. The liquid sample preparation section 10A, filter section 10B, and output section 10C operate under control and direction of controller section 10D. Preferably controller section 10D controls both the operation of system 10 and appraises and reports detection data D.

In one embodiment, the liquid sample preparation section 10A includes an electrospray head, which receives, conditions, and ionizes liquid sample S. This is transported to a preferred planar DMS filter in section 10B, the latter filtering the delivered ions and passing ion species of interest to output section 10C. In various embodiments of the invention, function in output section 10C may include immediate detection of ion species or transfer of ions to another component such as a mass spectrometer (MS) for detection of ion species thereat, with a readout being available of data D indicative of detected ion species.

As will be understood by a person skilled in the art, while a DMS filter with planar surfaces is illustrated, other configurations may be operable with various non-planar parts and surfaces, including filters, detectors, flow paths, electrodes, and the like.

Figure 2:
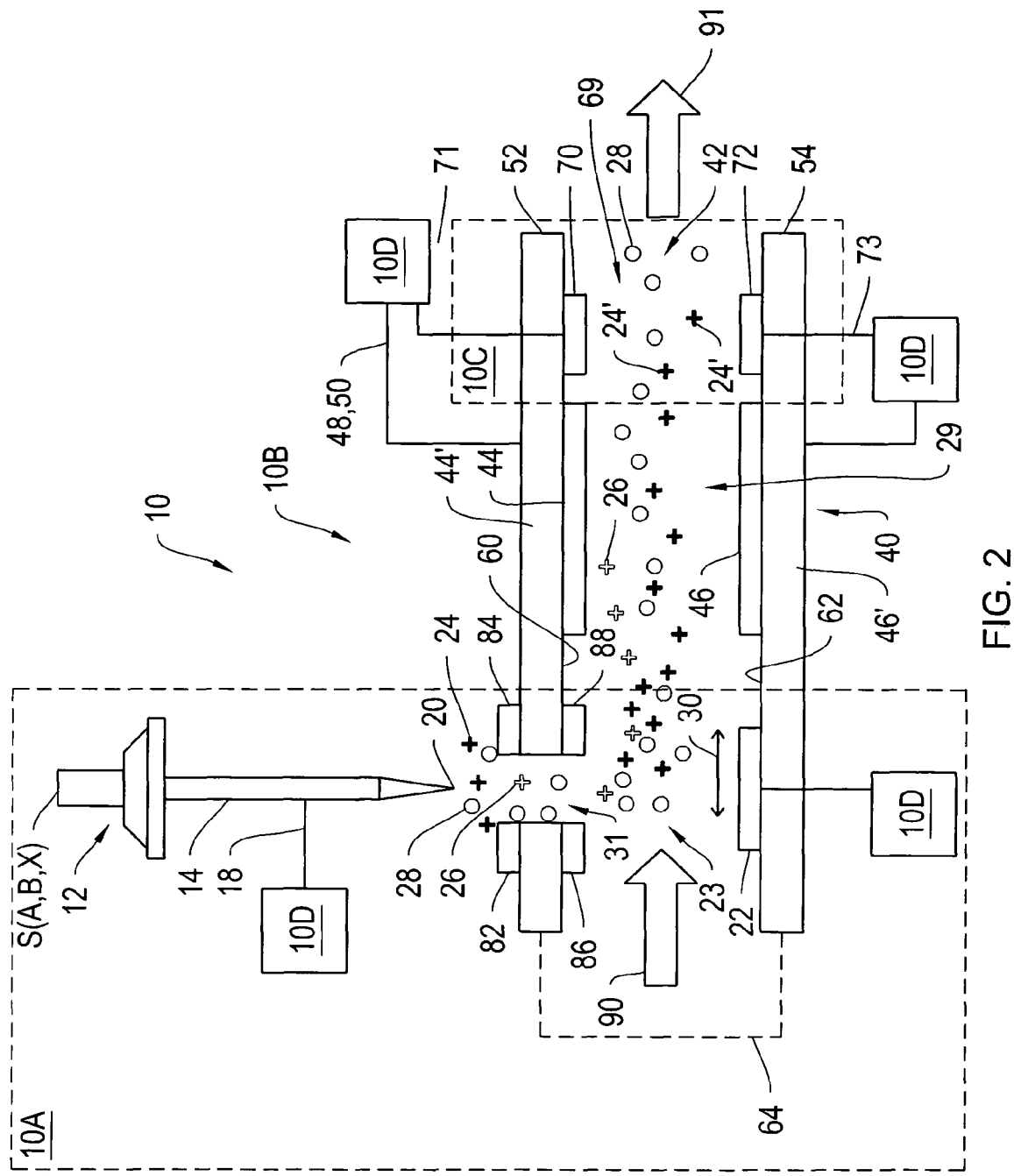
FIG. 2 shows a chemical sensor system with liquid sample preparation section including an electrospray source according to an illustrative embodiment of the invention.
Figure 3C:
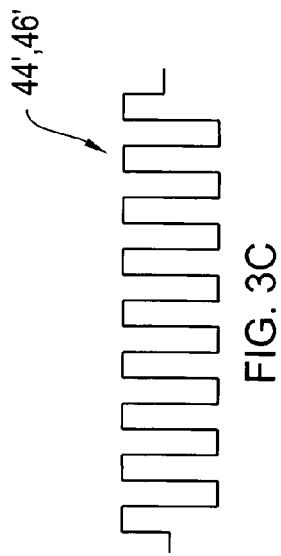
FIG. 3C shows a serpentine electrode according to an illustrative embodiment of the invention.

In the embodiments of FIGS. 2 and 3A, liquid sample preparation section 10A includes electrospray sample ionization source or head 12 having a chamber 14 for receipt of liquid sample S. In practice of the invention, the liquid sample S may contain bio-compounds, for example compounds A and B, in a solvent X. The present invention is engaged to identify one or more of the compounds in the liquid sample.

In practice of the electrospray device of section 10A, a high voltage potential 18 is applied by controller 10D to the liquid sample S within chamber 14 of electrospray head 12. The potential difference between the liquid sample S at electrospray tip 20 and attraction electrode 22, driven by controller 10D, ionizes compounds A, B in solvent X in sample S in ion region 23. This creates ions 24 and 26, representing compounds A and B, and solvent molecules 28. In one embodiment, ions and solvent are driven or drawn along flow path 30 into filter section 10B between the parallel filter electrodes 44, 46 of planar DMS ion filter 40.

Filtering in the planar DMS filter device 40 is based on differences in ion mobility, which is influenced by ion size and shape, among other items. This enables separation of ion species based on their characteristics. In one practice of the invention, a high intensity asymmetric waveform radio frequency (RF) signal 48 and a DC compensation signal 50 are applied to filter electrodes 44, 46 by RF/DC generator circuits within controller 10D. The asymmetric field alternates between a high and low field strength condition that causes the ions to move in response to the field according to their mobility. Typically the mobility in the high field differs from that of the low field. This mobility difference produces a net transverse displacement of the ions as they travel longitudinally through the filter between the filter electrodes. In the absence of a compensating bias signal, these ions would hit one of the filter electrodes and be neutralized. In the presence of a selected compensating bias signal 50 (or other compensation), a particular ion species will be returned toward the center of the flow path and will pass through the filter. Therefore, in the presence of the compensated asymmetric RF signal 48, separation of ions from each other according to their species can be achieved. Unselected species will hit the electrodes and be neutralized and species of interest will be passed through the filter. The data and system controller 10D regulate the signals 48, 50 applied to the filter electrodes 44, 46, in order to select which ion species pass through the filter.

It will be appreciated that it is desirable to isolate ions 24 and 26 to be able to obtain unambiguous identification of either or both of compounds A and B, as can be achieve with the planar DMS filter 40. The planar DMS filter 40 discriminates between ions A and B based on their mobility, such that in principle only one or the other is presented for detection at output section 10C according to the compensation applied by controller 10D. For example, ions 24 are shown as ions 24' passed by filter 40 in FIGS. 2 and 2.

Referring again to FIGS. 2 and 2, the output section 10C includes detector 69 with detector electrodes 70, 72. Controller 10D measures the current on electrodes 70, 72 as an indication of ions passed by filter 40. These electrodes are held at a potential by bias signals 71, 73, from controller 10D. Ions 24' which passed filter 40 deposit their charge on a detector electrode 70, 72 under control of controller 10D, depending upon the polarity of the electrode and the control signals 71, 73 on the detector electrodes. Furthermore, by sweeping the compensation (i.e., the bias voltage), a complete spectrum of ion species in Sample S can be detected.

By intelligent control of controller 10D it is possible to select different operating regimes and as a result it is possible to target the filtering of ion species of interest. In practice of one embodiment of the invention, the asymmetric electric signal 48 is applied in conjunction with compensating bias voltage 50, and the result is that the filter passes desired ion species as controlled by electronic controller 10D. As well, by sweeping bias voltage 50 over a predetermined voltage range, a complete spectrum of ion species in sample S can be achieved.

In another embodiment, the asymmetric electric signal enables passing of the desired ion species where the compensation is in the form of varying the duty cycle of the asymmetric electric signal, without the need for compensating bias voltage, again under direction of the control signals supplied by the electronic controller. By means of these features, the apparatus is also tunable, i.e., it can be tuned to filter ion species, passing only desired selected species to the detector.

A further advantage of the invention is that the filter can pass multiple ion species with similar mobility but different polarity, and these can be detected simultaneously. If each detector electrode 70, 72 is held at a different polarity, then multiple ion species (having similar mobility but different polarity) that pass through the filter can be detected simultaneously. Detected ions are correlated with the applied control signals 48, 50 and potential bias signals 71, 73 to determine the species of detected ion(s) indicated at data D, FIG. 2.

This multi-functionality may be further understood by reference to output section 10C, such as in FIG. 2, where a top electrode 70 is held at a predetermined voltage at the same polarity as the ions of interest passed by filter 40 while bottom electrode 72 is held at another level, perhaps at ground. Top electrode 70 deflects ions 24' downward to electrode 72 for detection. However, either electrode may detect ions depending on the ion charge and polarity and the signal applied to the electrodes. Thus multiple ion species having similar mobility but different polarity that pass through the filter can be detected simultaneously by using top electrode 70 as one detector and bottom electrode 72 as a second detector, and using two different detector circuits in controller 10D, with two different outputs thus emitted. Detector 69 may thus detect simultaneously multiple species passed by the planar DMS filter 40, such as a gas sample including sulfur in a hydrocarbon gas background.

The electronics controller 10D supplies the controlling electronic signals to system 10. A control circuit could be on-board, or off-board, where the planar DMS device has a control part with at least the leads and contact pads shown in FIG. 4A that connect to the control circuit 10D. The signals from the controller are applied to the filter electrodes via such connections.

Figure 4A:
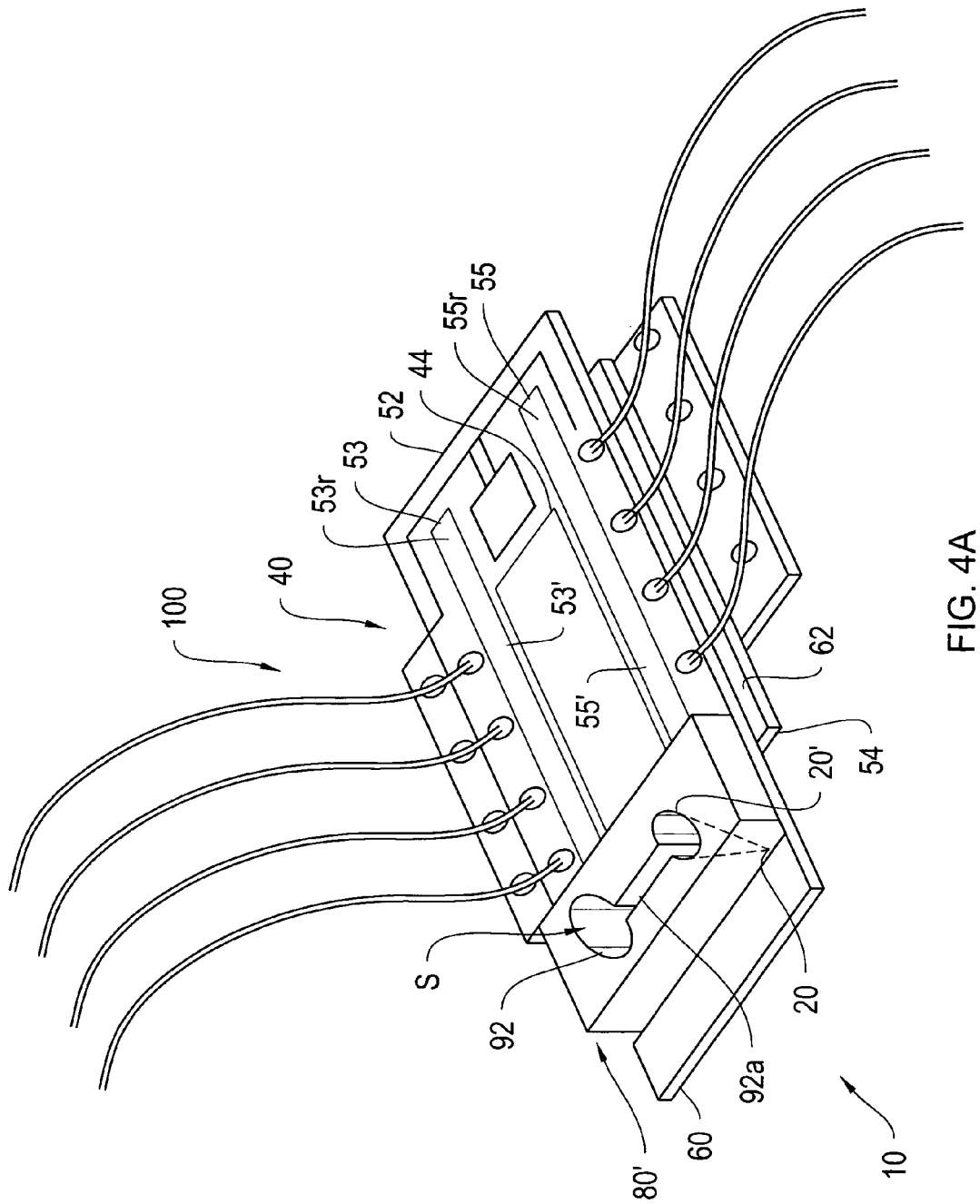
FIG. 4A shows a DMS spectrometer with spaced insulated substrates according to an illustrative embodiment of the invention.

In the embodiment of FIG. 4A, a planar DMS system 10 includes a spectrometer chip 100 having spaced insulated substrates 52, 54, (e.g., Pyrex® glass, ceramic, plastic and the like) with filter electrodes 44, 46 formed thereon (of gold or the like). Substrates 52, 54, define between themselves the drift tube 29 and flow path 30, thus performing a housing function. Preferably the substrates are insulating or have surfaces 60, 62 for insulated mounting of electrodes. Electrodes 44, 46 form ion filter 40, with the filter electrodes mounted on these insulated surfaces 60, 62 facing each other across the flow path 30.

Figure 4B:
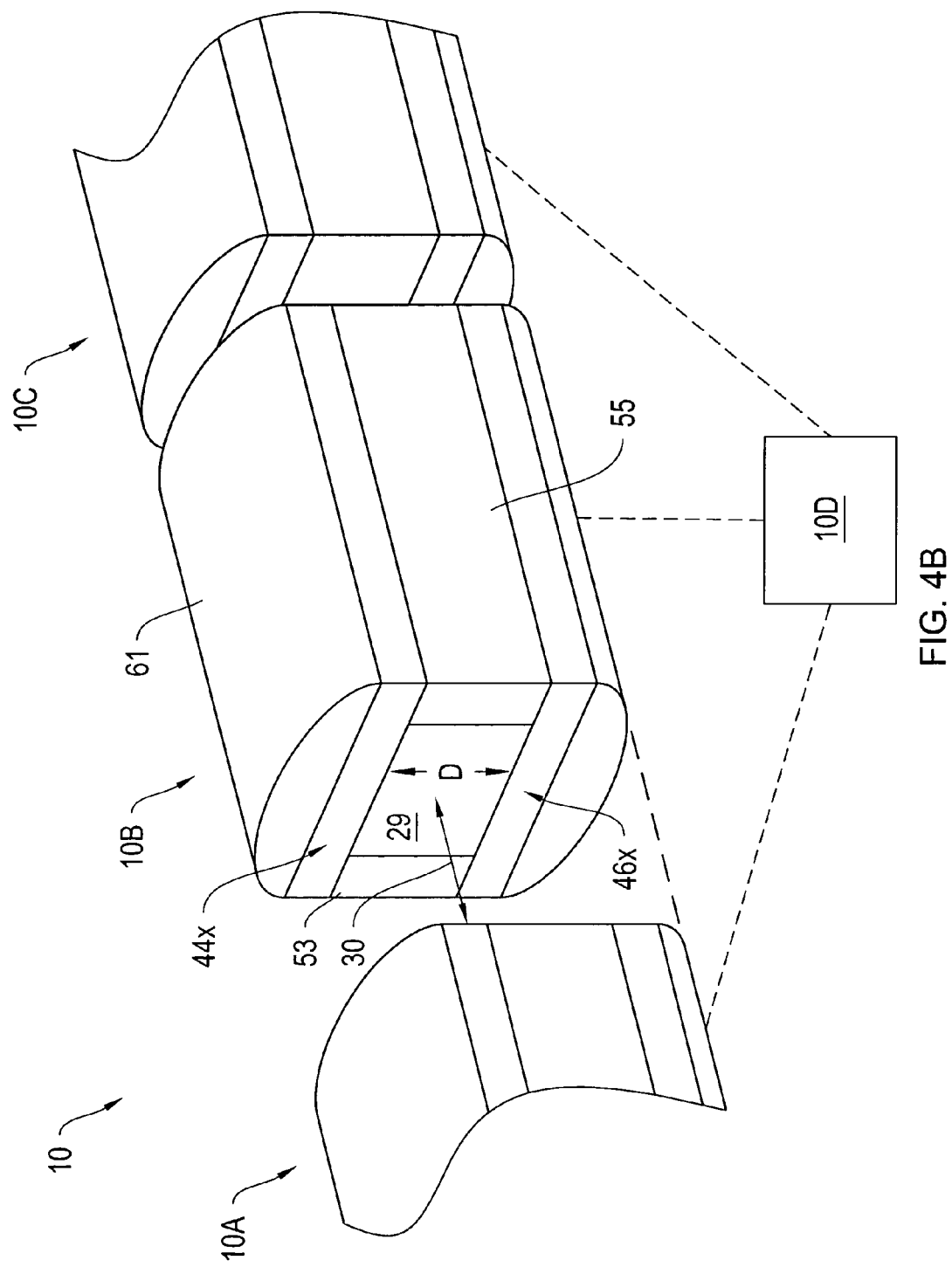
FIG. 4B shows an alternative structural electrode according to an illustrative embodiment of the invention.
Figure 4C:
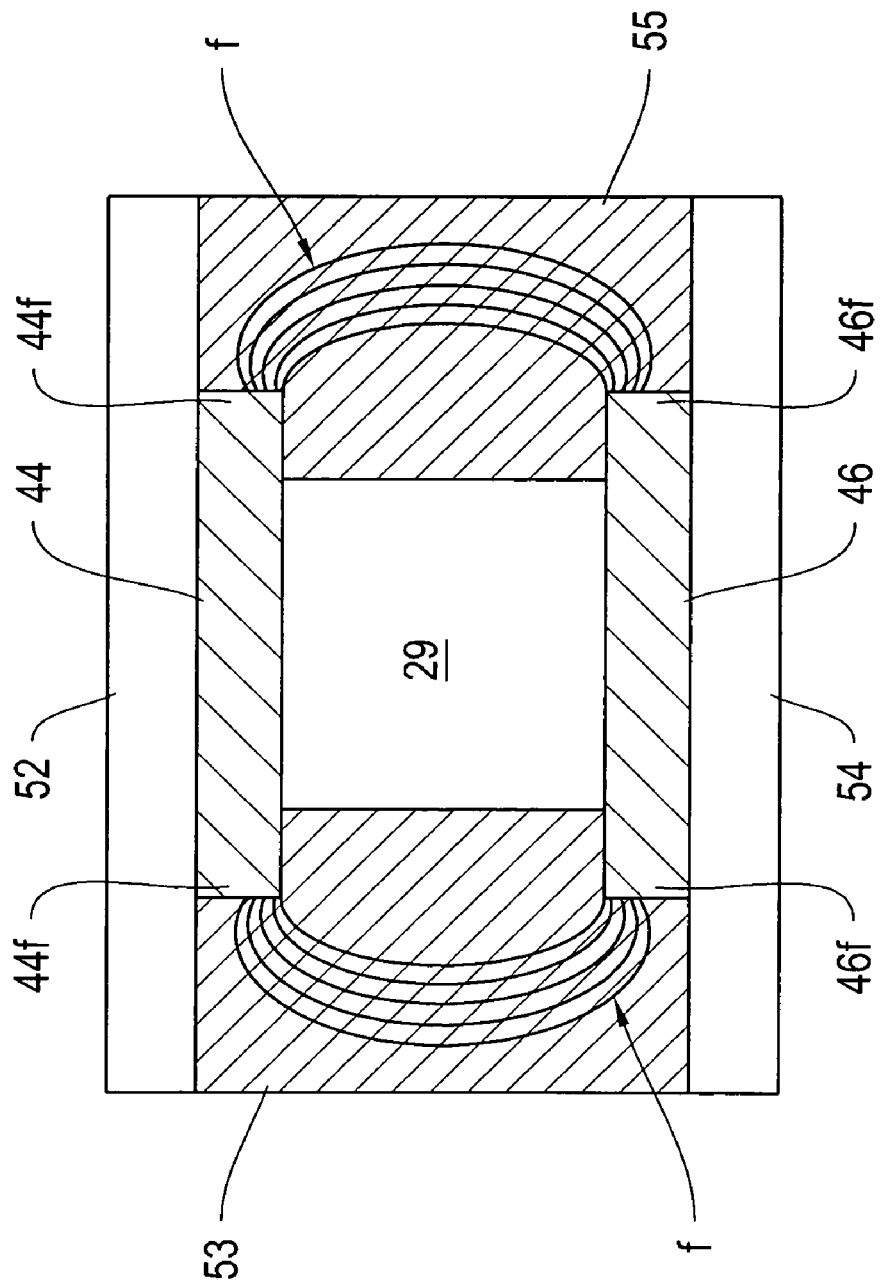
FIG. 4C shows side cross-sectional view of filter with insulating spacers overlapping edges of electrodes according to an illustrative embodiment of the invention.

As shown in FIG. 4A, 4B, 4C, substrates 52, 54 are separated by spacers 53, 55, which may be insulating and formed from ceramic, plastic, Teflon® or the like, or may be formed by etching or dicing silicon wafers, or creating an extension of the substrates 52, 54, for example. The thickness of the spacers defines the distance "D" between the faces of substrates 52, 54 carrying electrodes 44, 46. In one embodiment of FIG. 4A, the silicon spacers can be used as electrodes 53', 55' and a confining voltage is applied by controller 10D to the silicon spacer electrodes to confine the filtered ions within the center of the flow path. This confinement can result in more ions striking the detectors, and which in turn improves detection.

In a further alternative embodiment of the invention shown in FIG. 4B, alternative structural electrodes 44x, 46x, take the place of the substrates 52, 54, and are mounted at and separated by insulating spacers 53, 55, forming flow path 30 within. At one end of the flow path, sample preparation section 10A supplies the ions to the filter section 10B, and at the other end, the filtered ions pass into an output section 10C. In the same manner that the substrates serve a structure function and form a housing, so too the structural electrodes 44x, 46x serve the function of a housing, as well as being electrodes. As with the substrates, the outer surface of these electrodes may be planar or not, and may be covered by an insulated surface 61.

In the embodiment of FIG. 4C, shown in side cross-section, the insulating spacers 53, 55 overlap with the edges 44f, 46f of filter electrodes 44, 46. This ensures that the ions flowing in flow path (i.e., drift tube) 29 are confined to a region of uniform transverse electric field between the filter electrodes 44, 46, away from the electrode edges 44f, 46f where the non-uniform fringing field "f" is present. A further benefit is that all ions are forced to pass between the filter electrodes, and are subjected to that uniform field.

Figure 3D:
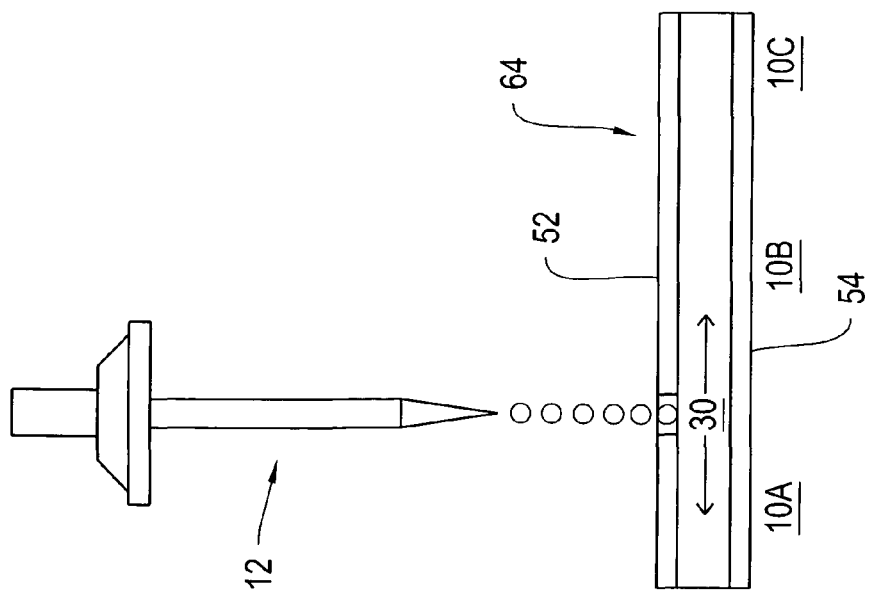
FIG. 3D shows the substrates forming a housing according to an illustrative embodiment of the invention.

Returning to FIG. 2, in operation, ions 24, 26 flow into the filter 40. Some ions are neutralized as they collide with filter electrodes 44, 46. These neutralized ions are generally purged by the carrier gas. Purging can also be achieved, for example, by heating the flow path 30, such as by applying a current to appropriately configured filter electrodes (e.g., serpentine 44',46' shown in FIG. 3D) or to resistive spacer electrodes. Spacer electrodes 53, 55 of FIG. 4A could be formed with resistive material and therefore could be used as heatable electrodes 53r, 55r.

Ions 24 are passed to output section 10C of FIG. 2. Exhaust port 42 is provided to exhaust the molecules 28 from the passed ions 24. This isolation of ions 24 eases the detection function and enables more accurate chemical analysis. But even with this precaution, some solvent molecules may remain attached to the ions of interest 24.

Therefore, in a preferred embodiment, apparatus is provided to desolvate ions such as 24 and 26 prior to their filtering. Desolvation may be achieved by heating. For example, any of electrodes 44, 46, 53r, 55r, may have a heater signal applied thereto by controller 10D. In another embodiment incoming gas flow may be heated by heater element 89 as shown in FIG. 3A.

It will be appreciated by those skilled in the art that desolvation or "drying" of electrosprayed ions is a critical part of the electrospray process. When the ion is first ejected out the electrospray tip it is in the form of a droplet with a large amount of solvent coating the ion. As it travels through the air towards a counter electrode the solvent evaporates eventually leaving the desolvated ion which can then be analyzed. Incomplete desolvation prior to analysis can distort the analysis. Additionally, a long ion travel distance may be required to allow the ion to sufficiently desolvate, without some other assistance. It will therefore be appreciated that this desolvation is beneficial in practice of the invention.

In another embodiment of the invention, a symmetric RF-electric field is used to enhance desolvation of ions produced in the electrospray prior to analysis. As shown in FIG. 5A, 5B, a symmetric radio frequency field applied perpendicularly to the carrier gas flow to cause the ions generated in the electrospray process to oscillate symmetrically, and be heated, as they travel down the drift tube so that the ions are desolvated without net deflection from this signal.

More particularly, the interaction between the ions and the neutral molecules raises their effective temperature, enhancing their desolvation. During their oscillations the ions will impact neutral air molecules and their internal temperature will increase. The rise in the internal temperature of the ions enhances the evaporation of the solvent and shortens the time to realize a desolvated charged ion. This action enables desolvation to be done over a relatively short length of the drift tube. Desolvation results in more accurate detection data, and the above approach is easily integrated with the PLANAR DMS filter of the invention.

The desolvating electric field can be generated by applying a voltage between two electrodes configured parallel to each other with a gap between them. For example, any of electrode pairs 44, 46 and 53, 55 may be used for this function, under control of controller 10D. Preferably separate desolvation electrodes 77, 79, as shown in FIG. 3A may be used for this function.

In a further embodiment of the invention, a micromachined electrospray head 80 is mounted on substrate 52, shown schematically in FIGS. 3A and 3B. Electrodes 82, 84, 86, 88 are formed on opposite sides of substrate 52 and guide the electrospray ions 24, 26 into ion region 23 of flow path 30 in drift tube 29. Attraction electrode 22 has a potential applied thereto to attract the ions 24, 26 into the ion region 23. Carrier gas flow 90 is set at a desired flow rate to capture ions 24, 26 and to carry them to filter 40 for the filtering function already described. The gas exhaust 91 includes the carrier gas 90 and carries away non-ionized components and neutralized ions.

Potentials applied to electrodes 22, 82, 84, 86, 88, and even desolvation electrodes 77, 79, can be set and controlled independent of each other and of the filter electrodes 44, 46. For example, this advantageously enables the attractor electrode 22 to be driven with a different signal than any other electrode, such as the adjacent filter electrode 46. This is particularly facilitated by provision of the insulated surfaces of the substrates, and the electrode isolation allows optimization of ion introduction independent of filter drive requirements.

This configuration also enables the guiding electrodes 82, 84, 86, 88 and attractor electrode 22 to be individually operated in a pulsed mode (e.g., switched on and off). In this mode, a select amount of ions can be introduced into the ion region 23. The time these ions travel, such as from the orifice to detector 72 for example, can be used in a "time-of-flight" ("TOF") DMS mode of operation. In this mode, the time of flight is associated with ion species, thus providing additional information for species discrimination. This leads to an improvement in cylindrical DMS devices.

As will be appreciated by a person skilled in the art of IMS, this TOF is an analog to the time-of-flight practiced in IMS devices, but now being practiced within a DMS structure. This new innovation may therefore provide both IMS and DMS detection data in one operating device; the combination of DMS and IMS data can yield better detection results.

In preferred embodiments, such as shown in FIGS. 2-3A, 4A-4B, the housing 64 is formed by substrates 52, 54, with internal flow path 30 defined extending from the input part 10A, through the ion filter 10B, to the output part 10C. More particularly, substrates 52, 54 present work surfaces 60, 62, which favor formation of electrodes thereat. These surfaces 60, 62 may be curved or planar and preferably insulating (or insulated), such as when formed using glass or ceramic substrates for example. This lends itself to mass manufacturing techniques such as Micro-Electro-Mechanical Systems (MEMS) or Multi-Chip Module (MCM) or other processes, with a result of very compact packaging and small electrode sizes. As such, the ion filter is preferably defined on these insulated surfaces by the facing filter electrodes 44, 46 with the flow path 30 defined in between, and the insulated surfaces of the substrates in turn then isolating the control signals 48, 50 at the filter electrodes from detector electrodes 70, 72, for lower noise and improved performance. This is unlike the extensive conductive area of the outer cylinder of conventional prior art DMS devices, such as in U.S. Pat. No. 5,420,424, incorporated herein by reference.

Figure 6:
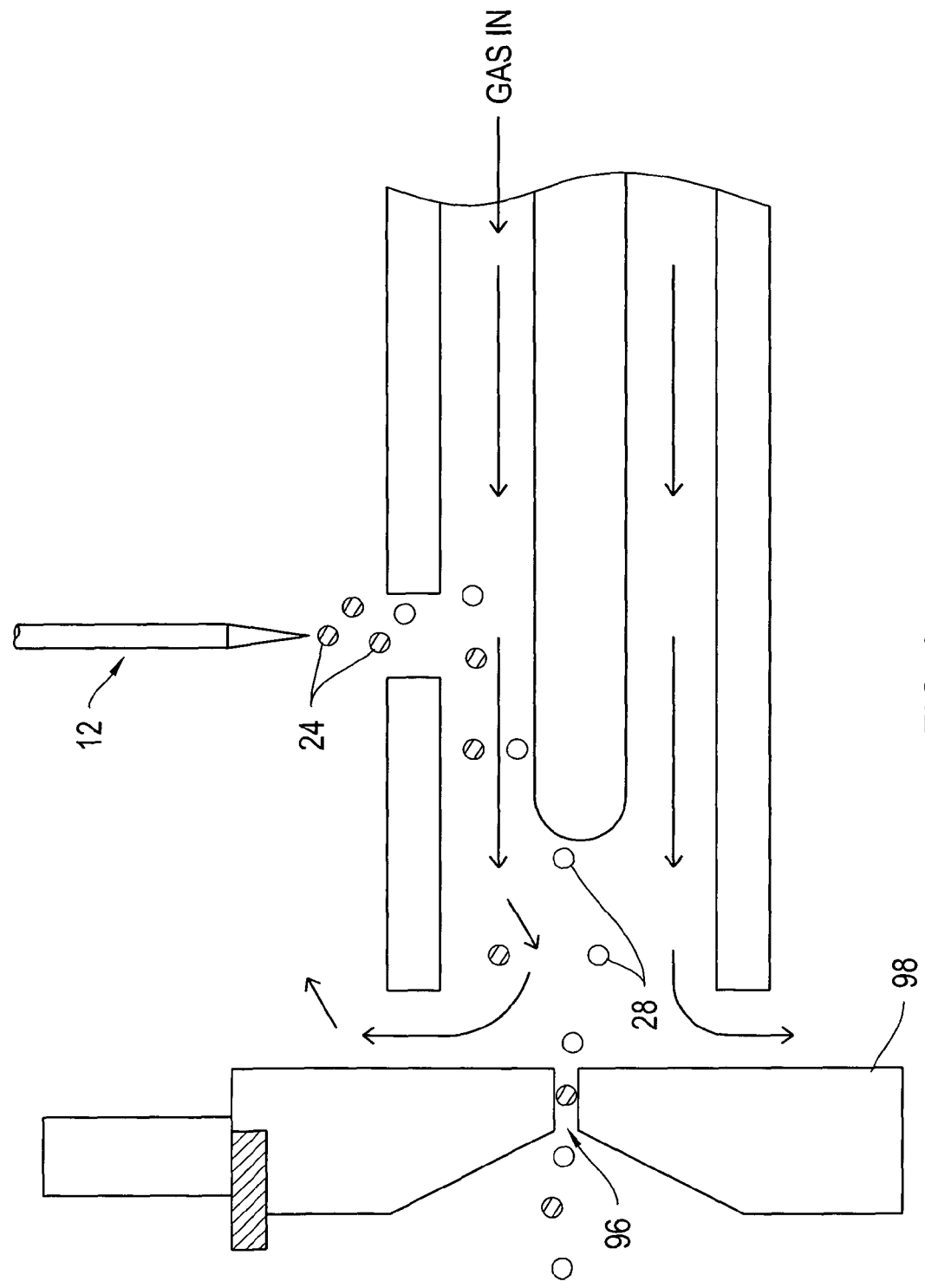
FIG. 6 shows a prior art cylindrical DMS connected to a mass spectrometer.

It will be further understood that due to geometrical and physical considerations, the ions in prior art cylindrical designs are distributed in the drift tube cross-section and therefore only a fraction of ions are available in the region R near the mass spec inlet 96. In the prior art configuration of a cylindrical DMS shown in FIG. 6 (see PCT/CA99/00715, incorporated herein by reference), an attempt is made to overcome this limitation by enabling additional delivery of ions to the mass spectrometer inlet 96. However neutral sample molecules can also enter into the mass spectrometer inlet 96 because there is no separation between the sample ions 24 and neutral molecules, such as solvent molecules 28. This leads to significantly more complex spectra in the mass spectrometer, and degraded resolution.

The present invention overcomes these shortcomings in the configuration of FIG. 3A, for example. In practice of the invention, virtually all of the ions 24 entering the detector region 69 are focused into the mass spec inlet 96. This results in a dramatic increase in efficiency of detection and improved sensitivity of the system, especially compared to a cylindrical DMS device where ions are distributed around the entire flow path circumference, not just at the MS inlet.

Furthermore, referring to a new cylindrical design of the present invention, shown in FIG. 7A, electrospray tip 20 injects samples via orifice 31' in outer electrode 44C into flow channel 30', under attraction of attractor electrode 22', and the sample is carried by the flow of gas G toward the filter section 10B'. The attractor electrode is formed adjacent to the inner electrode 46C but electrically isolated by insulator strips In1, In2. Therefore the attractor electrode can be independently biased separate from neighboring electrodes, e.g., 46C. This embodiment also combines functional and structural components while reducing parts count, such as where the inner cylinder components can be mated together via a binding function of the insulating layers In1, In2, for example.

Figure 7B:
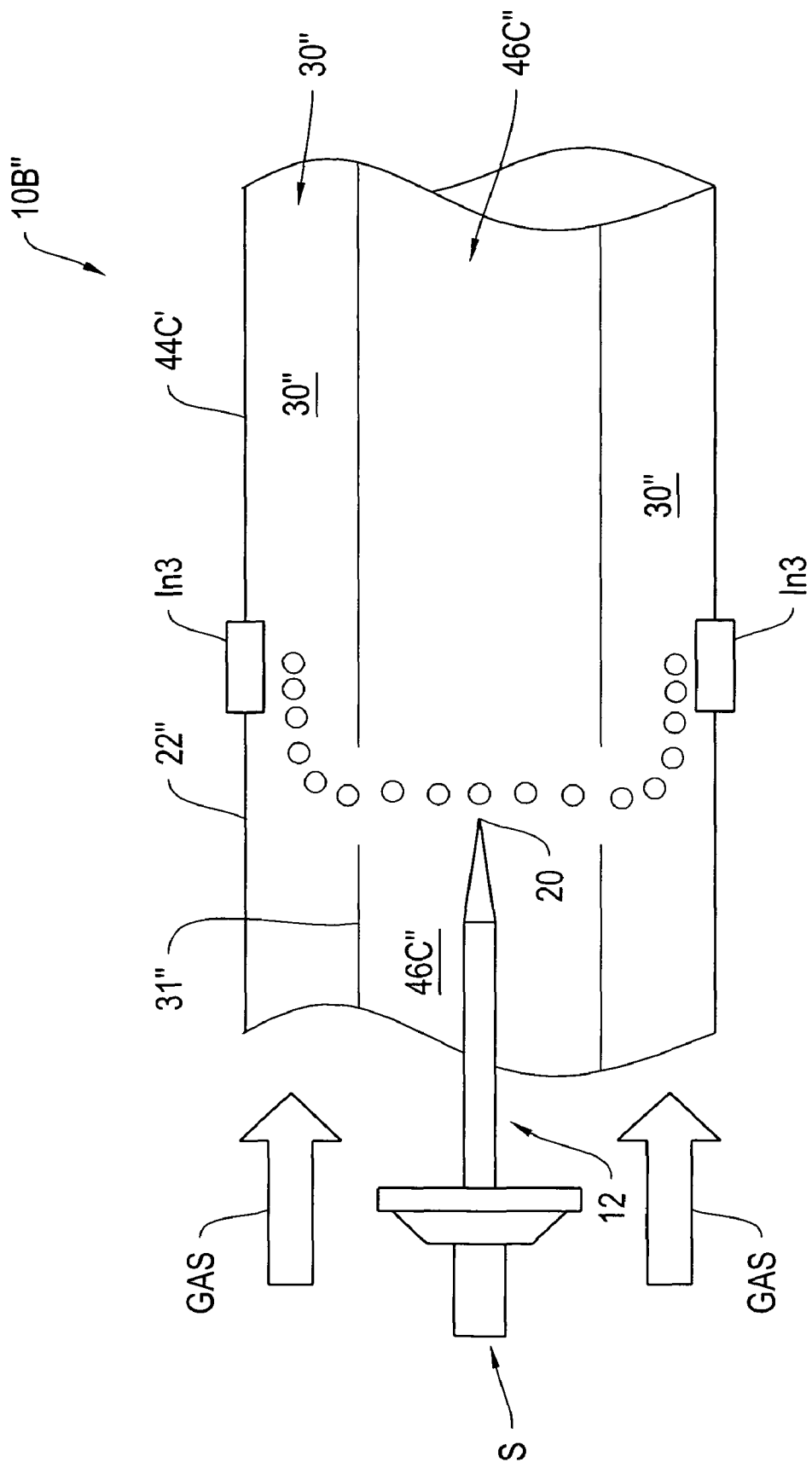

In an alternative embodiment shown in FIG. 7B, an attractor electrode 22" is formed adjacent to outer ring electrode 44C', insulated therefrom by insulator ring In3. The electrospray tip 20 introduces sample S from the side into the interior of a ring 46C", which may be a separate electrode, or may be an extension of inner electrode 46C', with the sample under attraction of attractor electrode 22" and being carried by gas G in flow channel 30" of filter section 10B". Again, electrode 22" is isolated from electrode 44C' by insulator In3, and therefore the electrodes are independently drivable.

Figure 8:
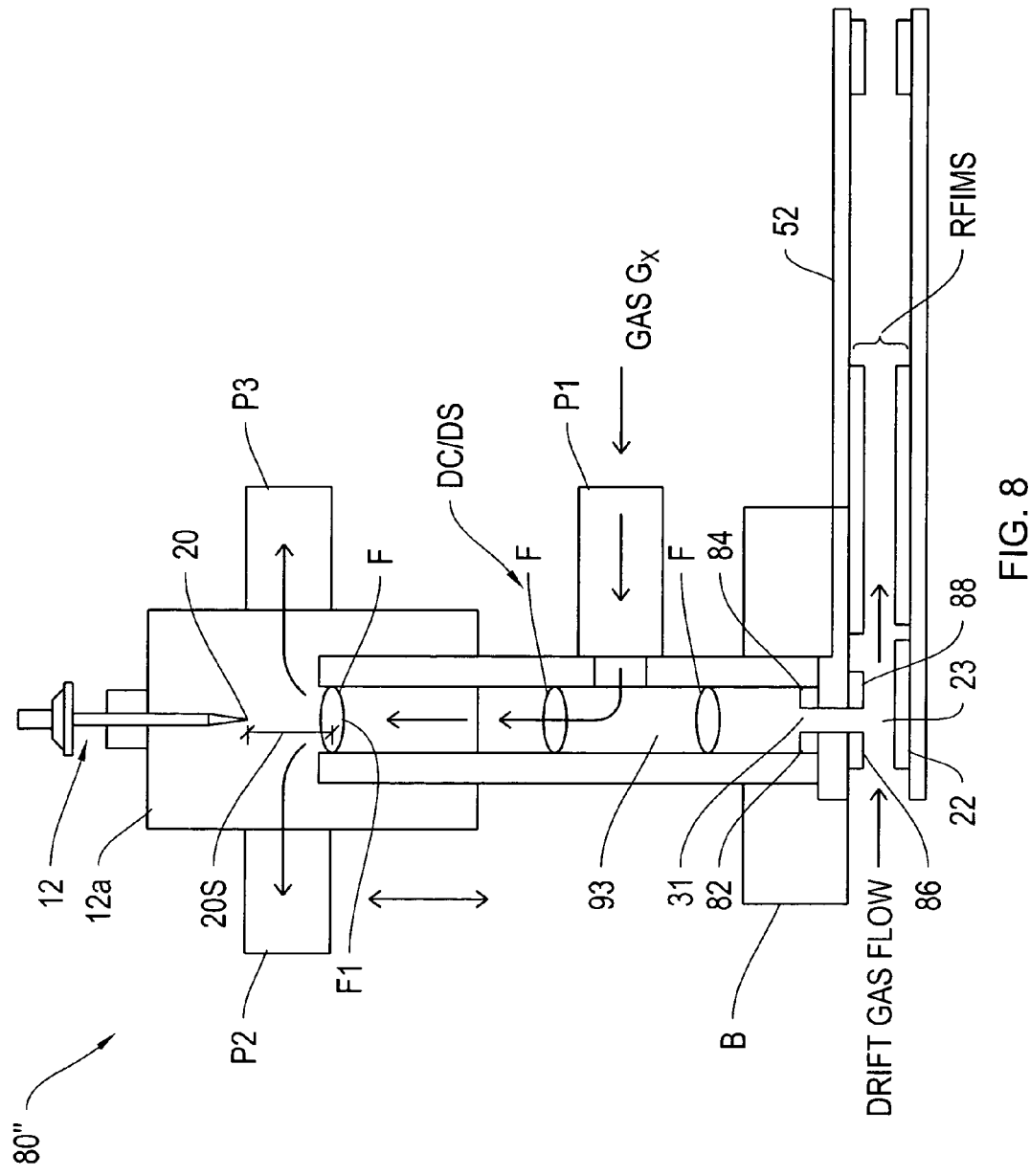
FIG. 8 shows an electrospray mounting tower according to an illustrative embodiment of the invention.

In a further embodiment of the invention shown in FIG. 8, electrospray assembly 80", attached to substrate 52, includes electrospray head 12. The ions are carried by guiding electrodes "F" (three in this embodiment), toward orifice 31 and are attracted into ion region 23 by attraction electrode 22 and guiding electrodes, such as 82, 84 and/or 86, 88.

Preferably a separate DC bias "DC" is applied to each guiding electrode to create a potential gradient which guides the ions towards ion region 23. The guiding electrodes can be used for a further function by also applying symmetric RF signals "DS" to enhance desolvation, as earlier discussed.

Cleansing gas G is introduced at port P1 to further enhance desolvation. This gas flows opposite to the guided ions in chamber 93 and exhausts out ports P2, P3. Preferably, this is operated with no pressure gradient across orifice 31.

In order to improve spray conditions, the separation 20S between the tip 20 and the top guiding electrode F1 can be adjusted in practice of the invention. In one practice, the position of housing 12a can be adjusted relative to base B, which in turn adjusts the separation 20S. In an alternative, the height of head 12 can be adjusted relative to electrode F1.

Figure 9A:
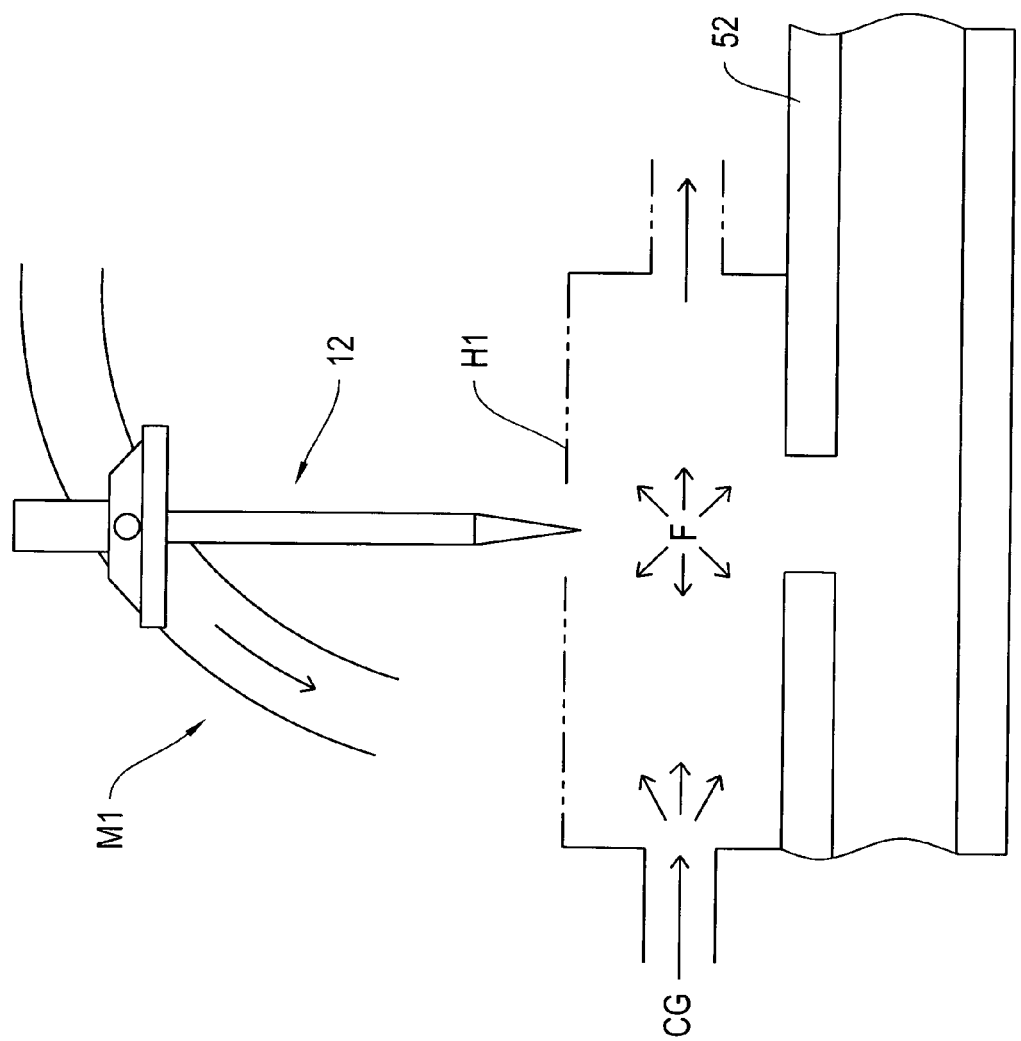
FIG. 9A shows an electrospray head cooperating with guiding electrodes according to an illustrative embodiment of the invention.
Figure 9B:
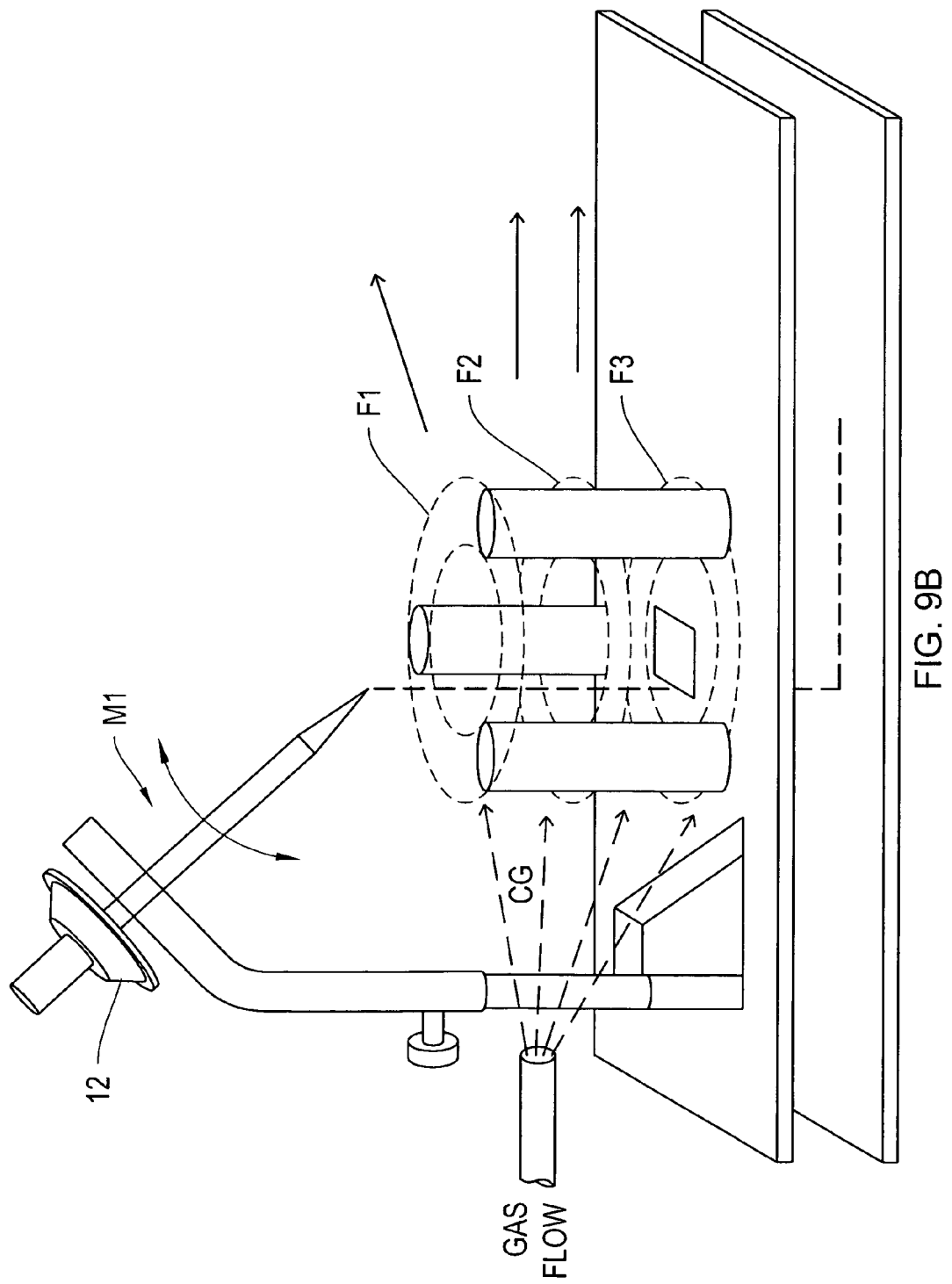
FIG. 9B shows an electrospray head cooperating with guiding electrodes according to an illustrative embodiment of the invention.

In an alternative embodiment, as shown in FIGS. 9A and 9B, spaced apart guiding electrodes F (FIG. 9A) or F1, F2, F3 (FIG. 9B) are bathed in a curtain gas flow CG. This flow may be unconfined or contained within housing H1. The electrospray head 12 is adjustably mounted in mount M1, wherein its angle of delivery can be adjusted relative to the surface of substrate 52. In addition, its height can be adjusted relative to the substrate.

Referring again to FIG. 4A, sample reservoir 92 receives a liquid sample S, which is then ionized and filtered as set forth above. In such embodiment, a single spectrometer chip 100 integrates both a ionization source, such as part of a microfluidic electrospray module 80', and planar high field asymmetric waveform ion mobility filter 40. An internal detector may also be included, or ions are outputted for detection. Various micro-fabricated micro-fluidic components may be used as an ion source, or combinations thereof, including electrospray, nano-electrospray, liquid chromatography, electrophoresis separation.

In another embodiment, the electrospray head 80' of FIG. 4A may be attached to substrate 52 (preferably through anodic bonding or brazing). Guiding electrodes 82 and 84 are not required in this embodiment.

Figure 4D:
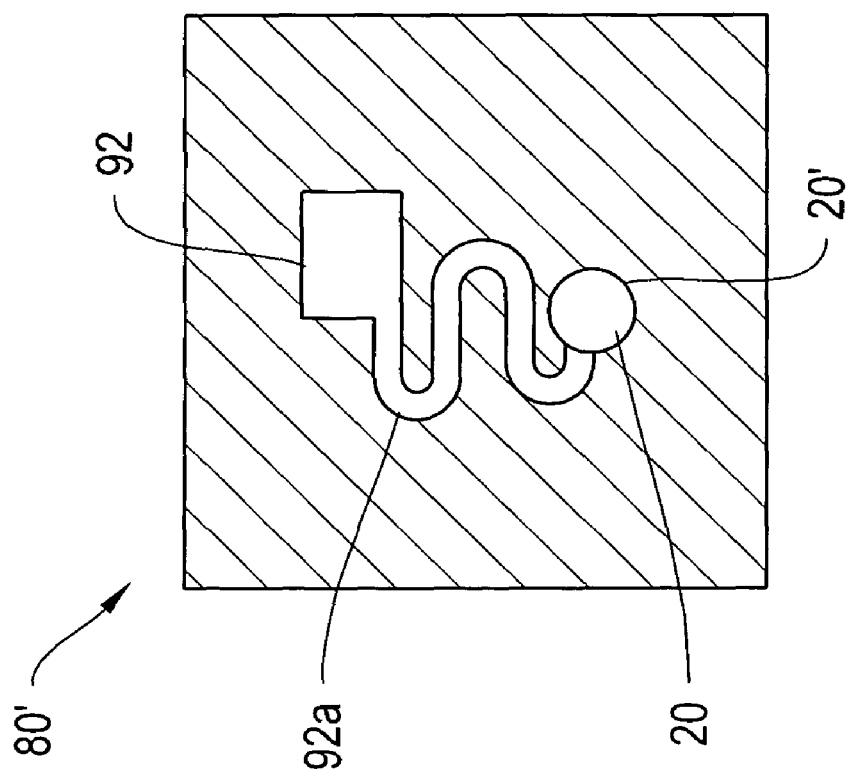
FIG. 4D shows an electrospray head with a sample reservoir feeding a separation channel leading to a spray tip according to an illustrative embodiment of the invention.

In the embodiment of FIG. 4D, the microfluidic electrospray module 80' includes sample reservoir 92 feeding a lengthened, serpentine, separation channel 92a, leading to tip orifice 20' and then to tip 20. The channel 92a may be a liquid chromatograph or electrophoretic separator, or the like, for conditioning or separating constituents in the sample prior to ionization at the tip 20.

The motivation for such a chip 100, with or without a microfluidic module, is to eliminate variability in sample preparation and analysis, this is achieved by reducing human interaction and by providing a device that incorporates all key components in a single structure. These chips 100 lend themselves to low cost manufacturing and as a result can be disposable. Using a new chip for each sample analysis eliminates sample to sample cross-contamination. Additionally, through the reduction in human intervention, sample preparation time is reduced. In a conventional arrangement the position of the electrospray tip or micro-fluidic component, must be re-adjusted each time relative to any filter or mass spectrometer inlet. This adds time and cost. With the integrated micro-fluidics chip/planar DMS apparatus of the invention, the relative positions of the micro-fluidic components and planar DMS inlet are fixed. Once analysis is completed the entire chip is simply discarded and a new chip is loaded with a sample to be analyzed and possibly to be mounted on a mass spectrometer. This allows for significantly faster analysis times and higher throughput.

Figure 10A:
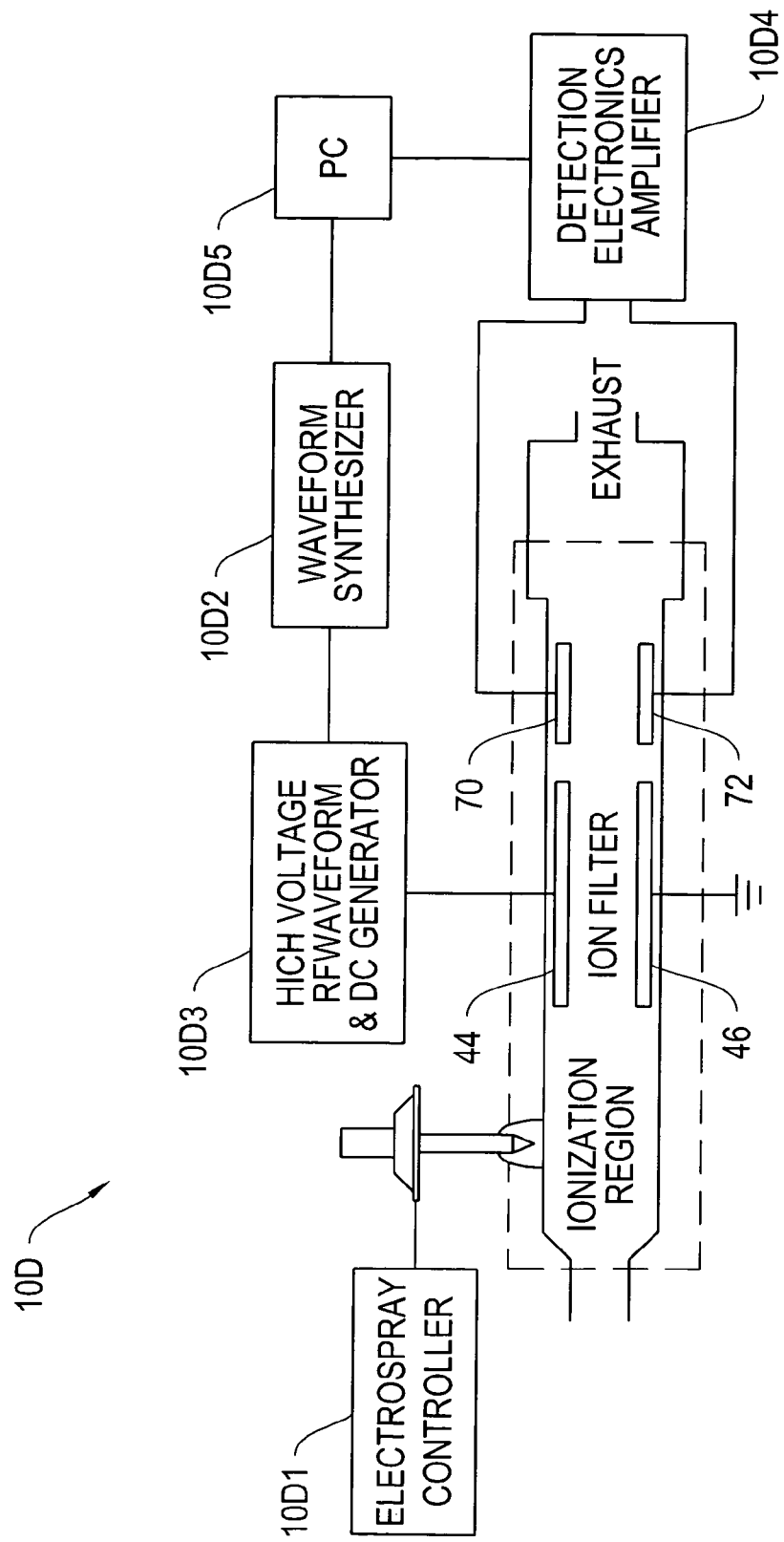
FIG. 10A shows the control system according to an illustrative embodiment of the invention.

In an illustrative embodiment of the invention, shown in FIG. 10A, controller 10D includes several subsystems, including an electrospray control 10D1, a waveform generator (synthesizer) 10D2 cooperating with high voltage RF waveform & DC generator 10D3 for applying the RF asymmetric drive signal and DC control bias to filter electrodes 44, 46, and detection electronics 10D4 for detection of ions on the detector electrodes. Computer 10D5 collects data and controls the system. In one embodiment, the RF field is produced in generator 10D3 by a soft-switched semi-resonant circuit that incorporates a flyback transformer to rapidly generate the high voltage pulses. The circuit provides a peak-to-peak RF voltage of at least 1400 volts at a frequency of around 100 KHz –4 MHz with a duty cycle of about 10-70%. Sample RF waveforms for driving the filter electrodes are shown in FIG. 10B, although variations thereof are also within practice of the invention.

Figure 11A:
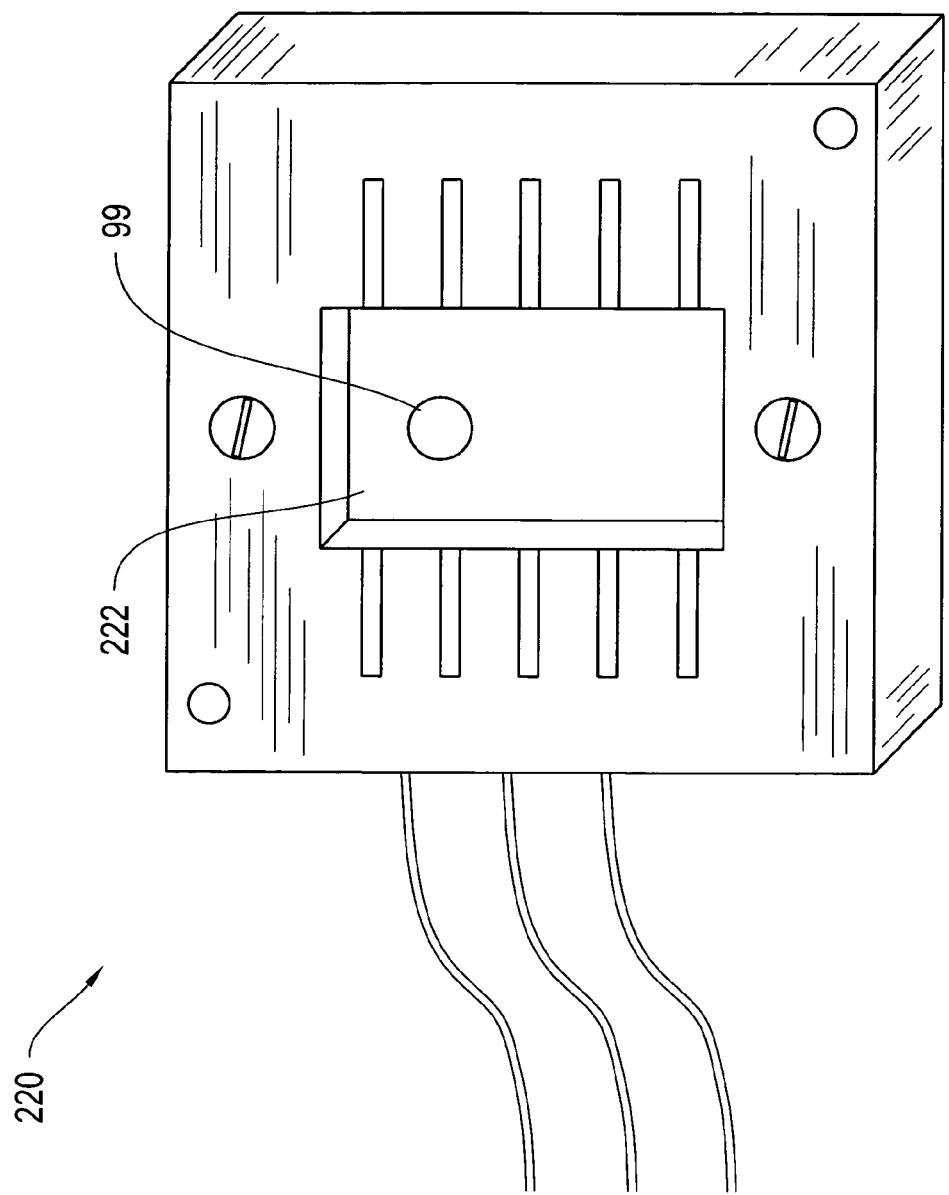
FIG. 11A shows a chip receptacle according to an illustrative embodiment of the invention.
Figure 11B:
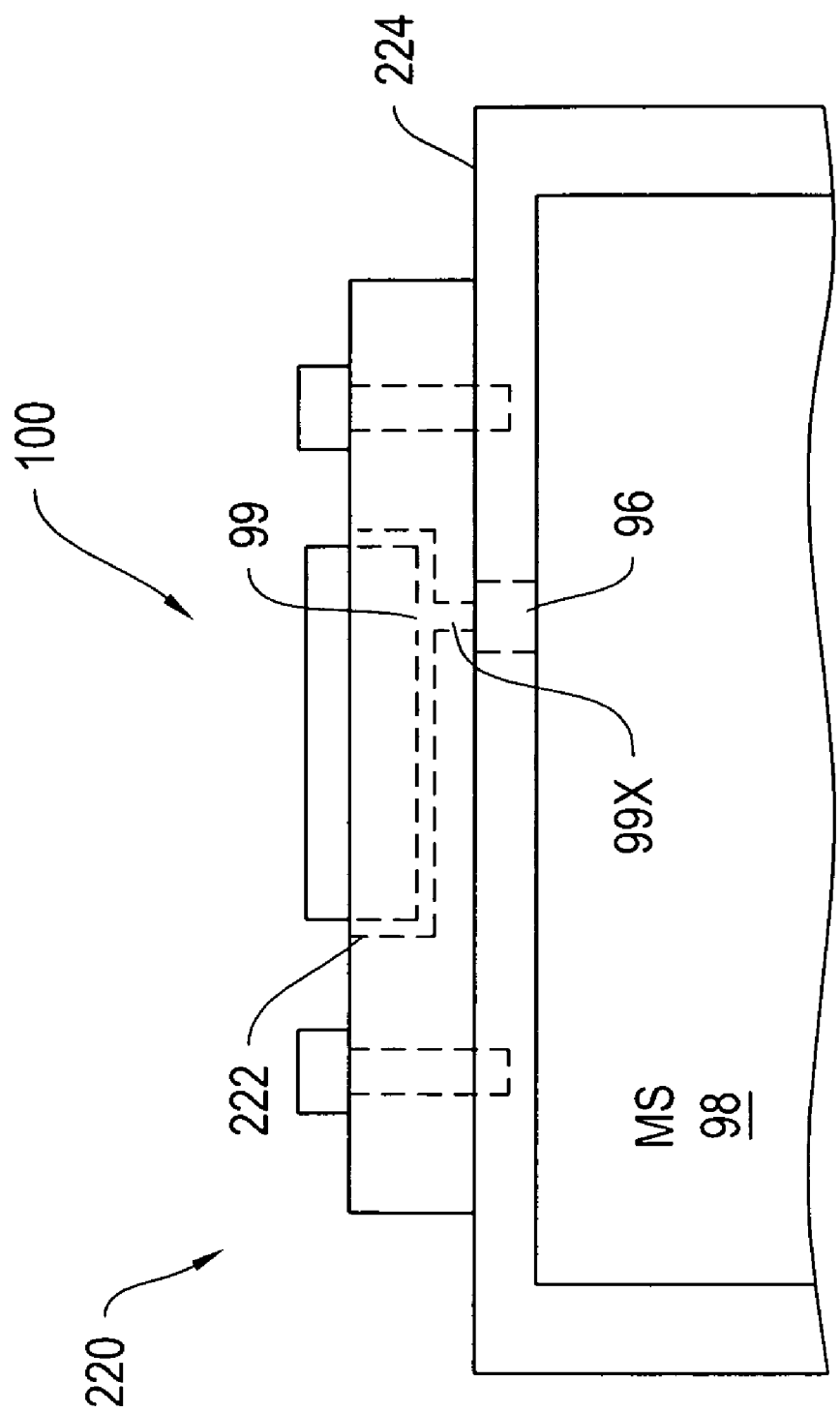
FIG. 11B shows a chip receptacle interfaced with a mass spectrometer according to an illustrative embodiment of the invention.

Preferably the chip 100 is inserted into a chip receiver assembly 220. Assembly 220 includes a socket 222 for receipt of the chip. The socket is electrically connected to the controller 10D. A preferred embodiment of chip receiver 220 serves a further function of coupling the chemical sensor system 10 to a mass spectrometer MS 98, as shown in FIG. 11B. Chip receiver assembly 220 is affixed to the face 224 of the mass spectrometer, such that outlet orifice 99 of system 10 is aligned via orifice 99x with the MS orifice inlet 96, whereby ions 24' are directed into the MS for detection and analysis.

Detection of ions 24 passing through filter 40 may be made as described above in conjunction with the detector electrodes 70, 72 of FIG. 2. An alternative embodiment is shown in FIG. 3A where electrode 70 is now used as a deflector electrode to deflect ions 24' toward intake 96 of mass spectrometer 98. The ions are guided or focused by focusing electrodes 72a, 72b and pass through an orifice 99 in substrate 54' and through plenum gas chamber 101 via a mounting adapter 102. Providing a low flow rate plenum gas into chamber 101 prevents neutralized sample ions or solvent molecules from entering the mass spectrometer intake 96. Ions that are focused into the mass spectrometer intake are then detected according to standard mass spectrometer procedures. It will be appreciated that the plenum chamber 101 is not shown in FIG. 11B, although it may be beneficially used in this embodiment.

An assembly of the invention can be easily mounted right up against the mass spectrometer inlet 96 (with or without a plenum chamber), as shown in FIGS. 3A, 11B and 12A-12B, for example. The deflector electrode (side mounting FIG. 3A or 12A-12B) allows almost 100% of ions to be deflected into the mass spectrometer.

This high efficiency is in contrast with the prior art cylindrical design in FIG. 12C-12D, mounted to inlet 96 of the mass spectrometer, where only a small fraction of the total ions in the drift tube are affected by the electric field which propels them into inlet 96 and resulting in only a fraction of the available ions being detected in the prior art.

It will now be appreciated that in practice of the invention, chemical analysis can be performed using any of several ion detectors. In the embodiments of FIGS. 2 and 4A, the detector is entirely internal to the assembly 10. In the embodiment of FIG. 3A, assembly 10 is intimately mated via adapter 102 to the mass spectrometer 98 as a detector. In the embodiment of FIG. 3A, if the current on focusing electrodes 72a, 72b is monitored, then additional detector information is available for processing the detection information of mass spectrometer 98. Even without focusing electrodes 72a, 72b, a DMS spectra of the invention can be reconstructed by monitoring the total ion current in the mass spectrometer.

Figure 13A:
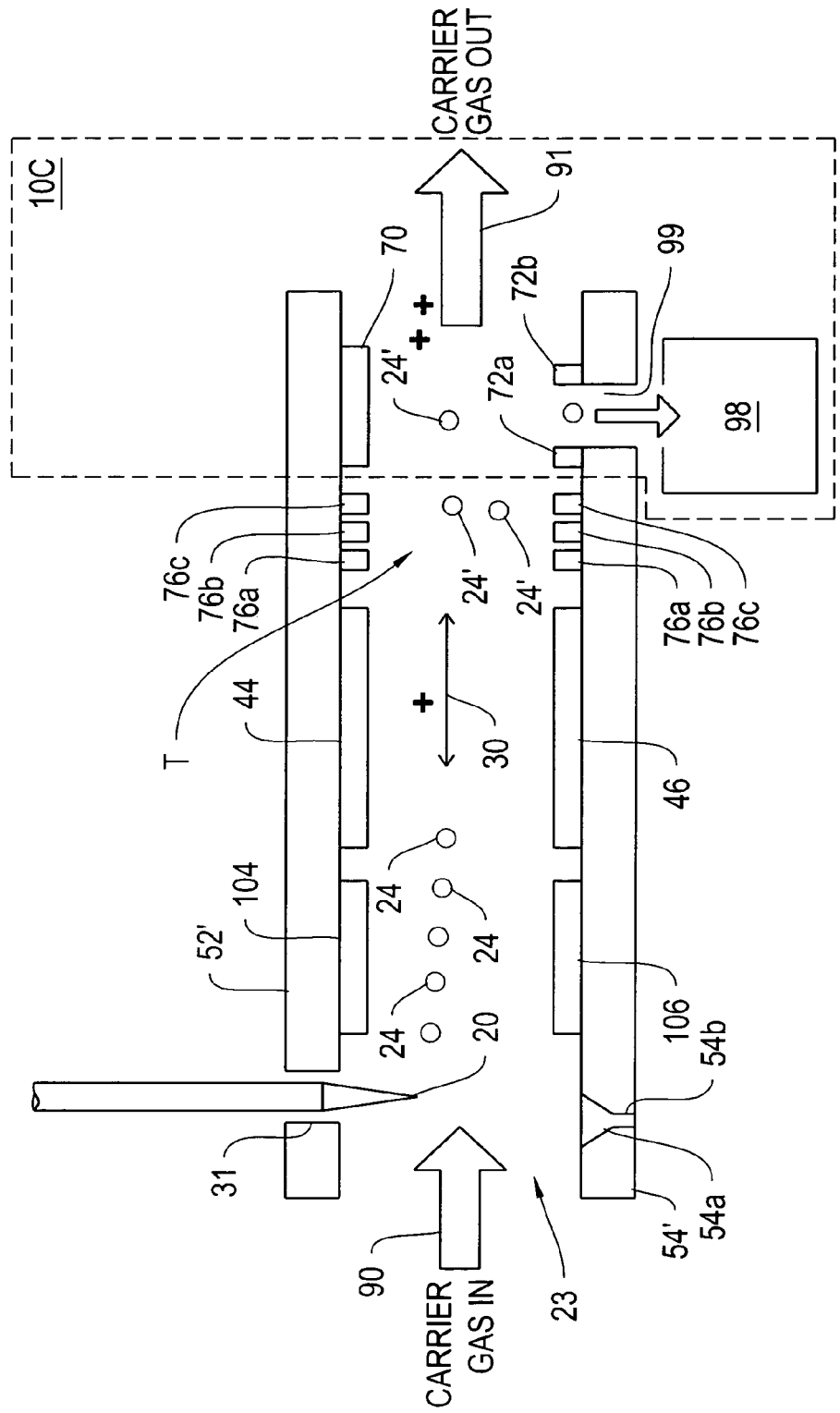
FIGS. 13A and 13B show an electrospray tip inserted within the ion region, either from above through orifice in upper substrate or from the side according to an illustrative embodiment of the invention.
Figure 13B:
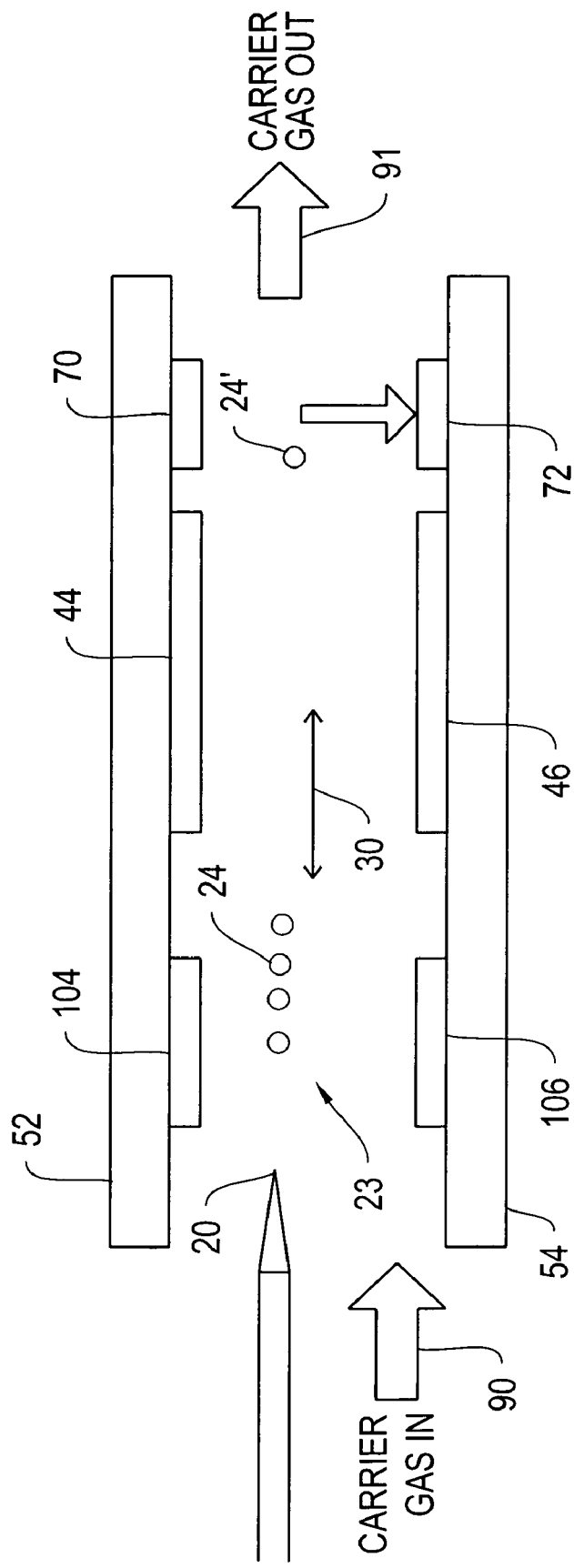

Alternative embodiments of the invention are shown in FIGS. 13A and 13B where the electrospray tip 20 has been inserted within ion region 23, either from above through orifice 31 in upper substrate 52' (FIG. 13A) or from the side (FIG. 13B). Attractor electrodes 104, 106 attract and guide the ions in the flow path 30 as they travel in gas flow 90 toward filter electrodes 44, 46. In FIG. 13A, droplets from the electrospray tip 20 collect in reservoir 54a, which also may be provided with a drain hole 54b.

It is desirable to concentrate ions after they pass through the ion filter and before entering output section 10C. This improves the signal to noise ratio at the detector and improves sensitivity. An ion trap or ion well can collect ions in this manner, concentrating them and then delivering the concentrated ions at once to the output section. Neutrals are not collected in the ion trap and are continuously being removed by the gas flow from the ion trap T.

An ion trap can be applied to many embodiments of the invention, such as in FIG. 2,B,C, for example. An illustrative embodiment is shown in FIG. 13A, where an ion trap T is formed with several appropriately biased electrode pair. In one example, for positive ions, the electrodes are biased such that a potential minimum is formed in the region of electrode pair 76b and potentials on electrode pairs 76a and 76c are higher. Ions are allowed to accumulate in the trap, and after a desired amount of time resulting in collection of a desired number of ions, the trap can be opened by adjusting the voltages applied to electrodes 76a, 76b and 76c. When the trap is opened, the trapped ions 24' flow into the output section 10C.

Figure 14A:
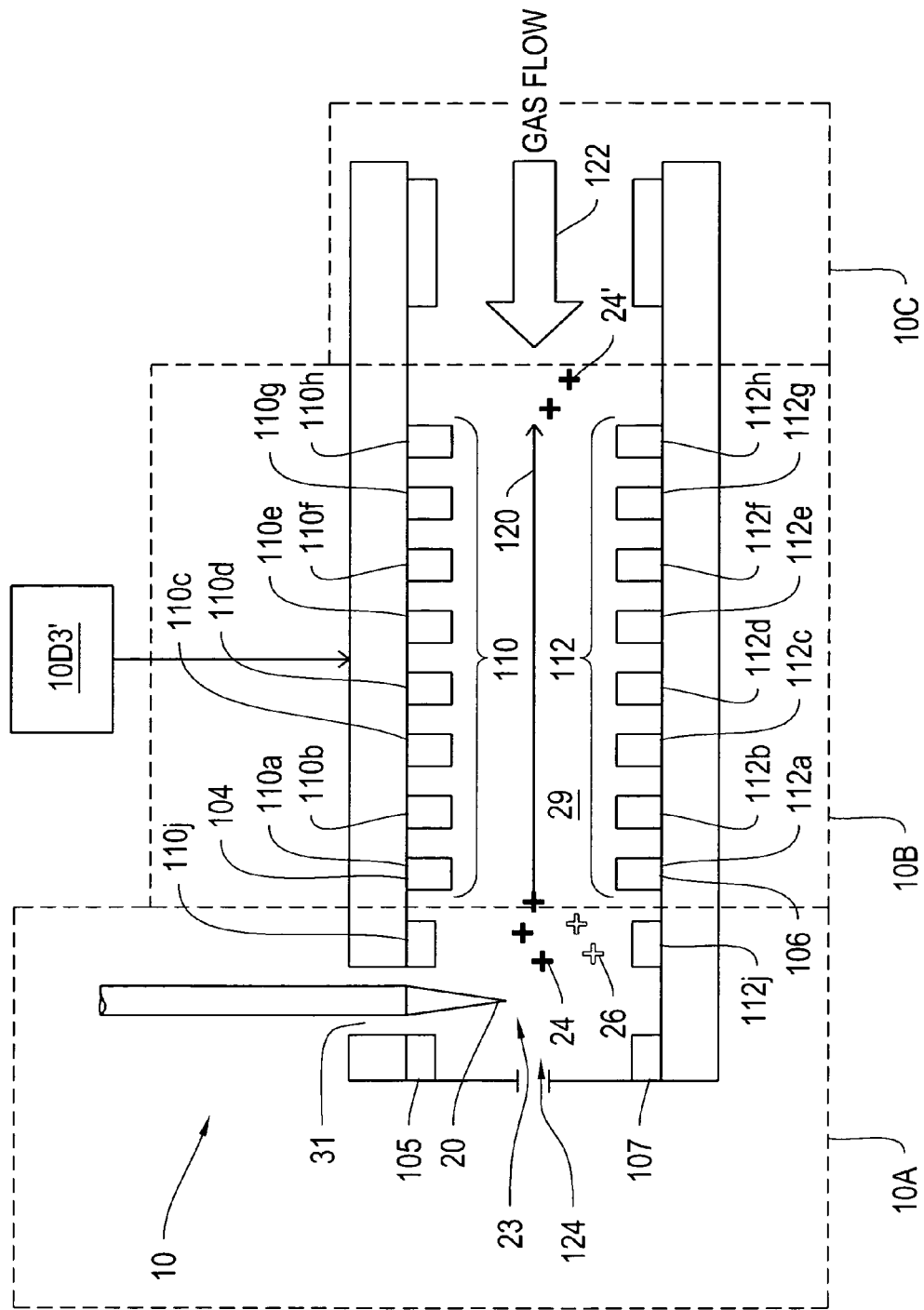
FIGS. 14A and 14B show longitudinal electric field driven embodiments according to an illustrative embodiment of the invention.
Figure 14B:
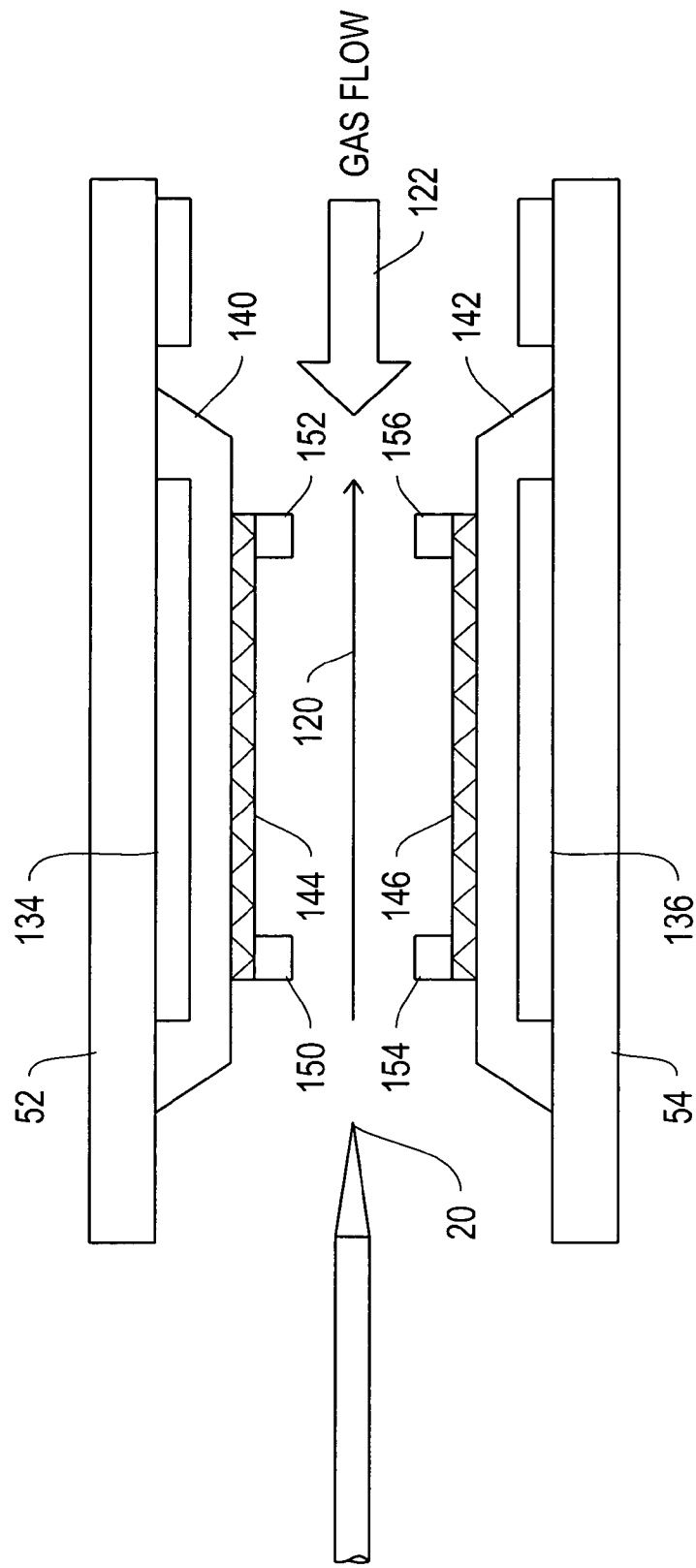

In the embodiments discussed above, ion filter 40 includes spaced electrodes 44, 46 which are driven by the RF and DC generator 10D3 as ions are propelled by gas flow 90 in drift tube 29. In the embodiment of FIGS. 14A and 14B, a longitudinal electric field driven embodiment of the invention, a novel method of conveying the ions in the drift tube 29 is shown.

In the embodiments of FIGS. 14A and 14B, the ions are propelled toward the output section 10C using a longitudinal electric field generated by electrodes 110 and 112. These embodiments feature a simplified gas flow structure in a very compact design, and gas flow is even optional.

In one embodiment, ions travel in an opposite direction to gas flow 122, and are propelled by electric field vector 120. This gas flow opposite to the ion travel direction enhances the desolvation of the sample ions. It also maintains a clean ion filter 40 free of neutral sample molecules. This consequently decreases the level of ion cluster formation resulting in more accurate detection of ion species. Furthermore the counter gas flow clears out and reduces memory effects of previous samples in ionization region 23. This embodiment can include integrated electrospray tip 20 inserted within ion region 23 from above, or side mounted, as are shown.

In the longitudinal electric field driven embodiments of FIGS. 14A and 14B, ions 24, 26 are conveyed without gas flow 122 but rather by action of a longitudinal electric field produced by sets of cooperating electrodes 110, 112 along with a longitudinal RF & DC generator 10D3'. As an example of the operation of the planar DMS in a particular electrode bias scheme, several or all of the electrode pairs 110a-h, 112a-h have the same RF voltage applied, while the DC potentials are stepped so that a longitudinal potential gradient is formed to drive the ions towards the detector. This embodiment can operate without a gas flow or optionally can include an exhaust gas flow 122 which exhausts neutrals and solvent molecules out exhaust port 124.

In one example, electrodes 110, 112a might have 10 vdc applied thereto and electrodes 110h, 112h then might have 100 vdc applied. Now negative ions in region 10A are attracted by electrode pair 110a-112a and further attracted by pair 110h, 112h, and their momentum then carries them into detector region 10C if passed by the filter.

The RF and compensation may be applied to various of the electrodes 110a-h, 112a-h, and will operate in the manner set forth above.

In another embodiment of FIG. 14A the electrospray tip can be external to ionization region 23 (not shown) above orifice 31 where electrode 112j serves as the attraction electrode. In the longitudinal electric field driven embodiment of FIG. 14B, the ion filter includes spaced resistive layers 144, 146 insulated from electrodes 134, 136, by insulating medium 140, 142, for example, a low temperature oxide material. Preferably the substrates are insulating. Resistive layers 144, 146 are preferably a ceramic material deposited on insulating layers 140,142. Terminal electrode pairs 150, 152, 154, 156 make contact with a resistive layer and enable a voltage drop across each resistive layer to generate the longitudinal electric field vector 120. Electrodes 150 and 154 are biased according to application, for example they may be at 1000 volts while electrodes 152 and 156 may be at zero volts.

When the embodiment of FIG. 14B is implemented in a cylindrical design, then the electrodes 150 and 154 form a ring electrode, and electrodes 152 and 156 form a ring electrode, and resistive layers 144, 146 form a cylinder.

The present invention can also perform time of flight ion mobility spectrometry functions. For example, in the embodiment of FIG. 14A, electrodes 104, 106 are pulsed to draw a sample from tip 20 that is ionized, starting the time cycle. Electrodes 110a-h, 112a-h are biased relative to their neighbors so that the ions are driven by the generated longitudinal electric field gradient towards output section 10C. A counter gas flow 122 can be applied to sweep sample neutrals away. A combination of these electrodes can be used to form the ion trap T described above (see FIG. 12).

Figure 15A:
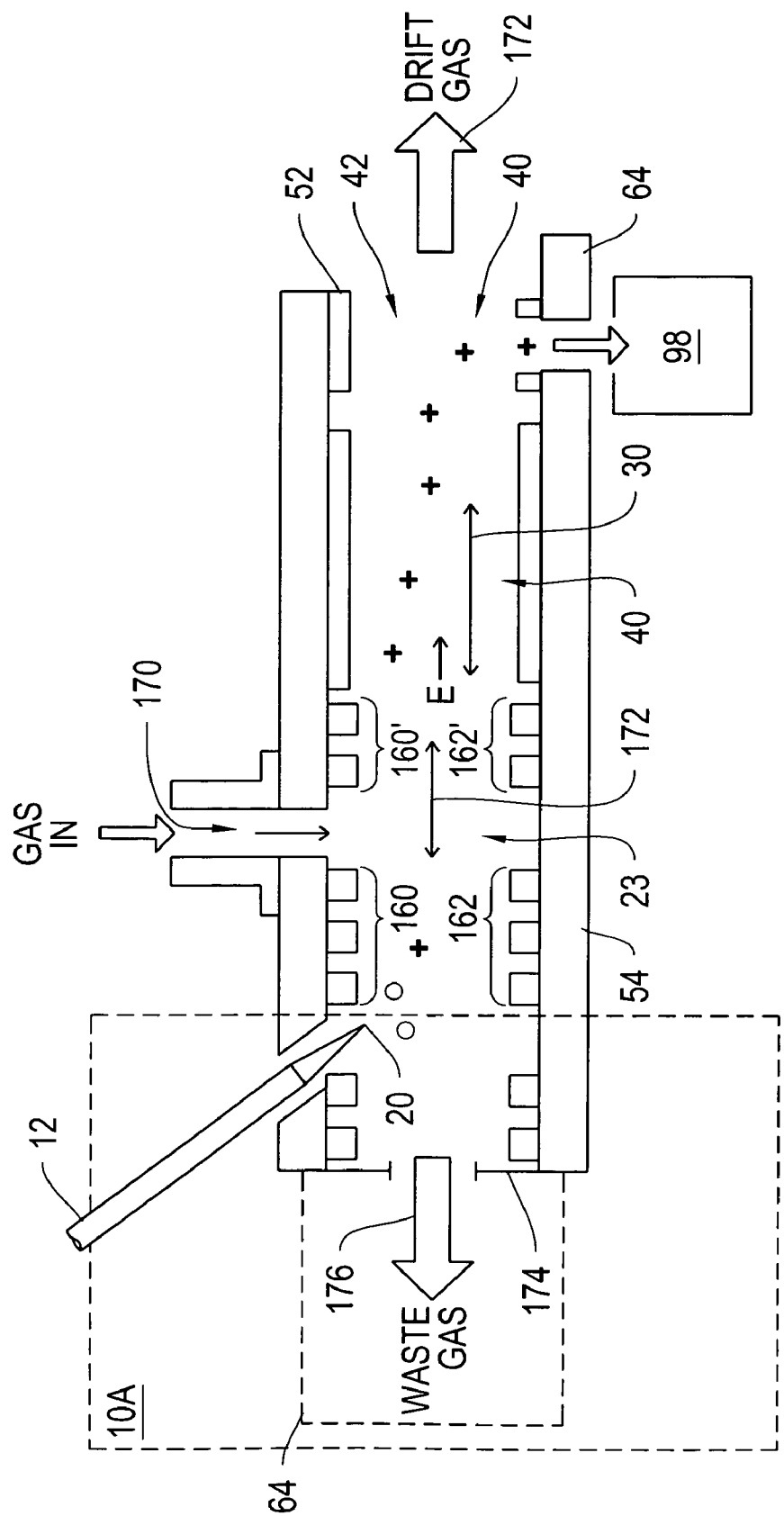
FIGS. 15A and 15B show split gas flow embodiments according to an illustrative embodiment of the invention.

In the split gas flow embodiment of FIG. 15A, the electrospray needle 12 is inserted through substrate 52 and into ion region 23, however, it may be mounted externally to the drift tube such as in FIG. 2. The ion flow generator in this design includes a plurality of segmented electrodes 160, 162 on opposite sides of flow path 30 to create longitudinal electric field E. In the preferred embodiment, one or more discrete electrodes 160', 162' are located downstream of gas inlet 170 to extend longitudinal electric field E beyond the split flow of gas, and thereby ensuring that ions flow into filter 40 as carried by drift gas flow stream 172.

Figure 15B:
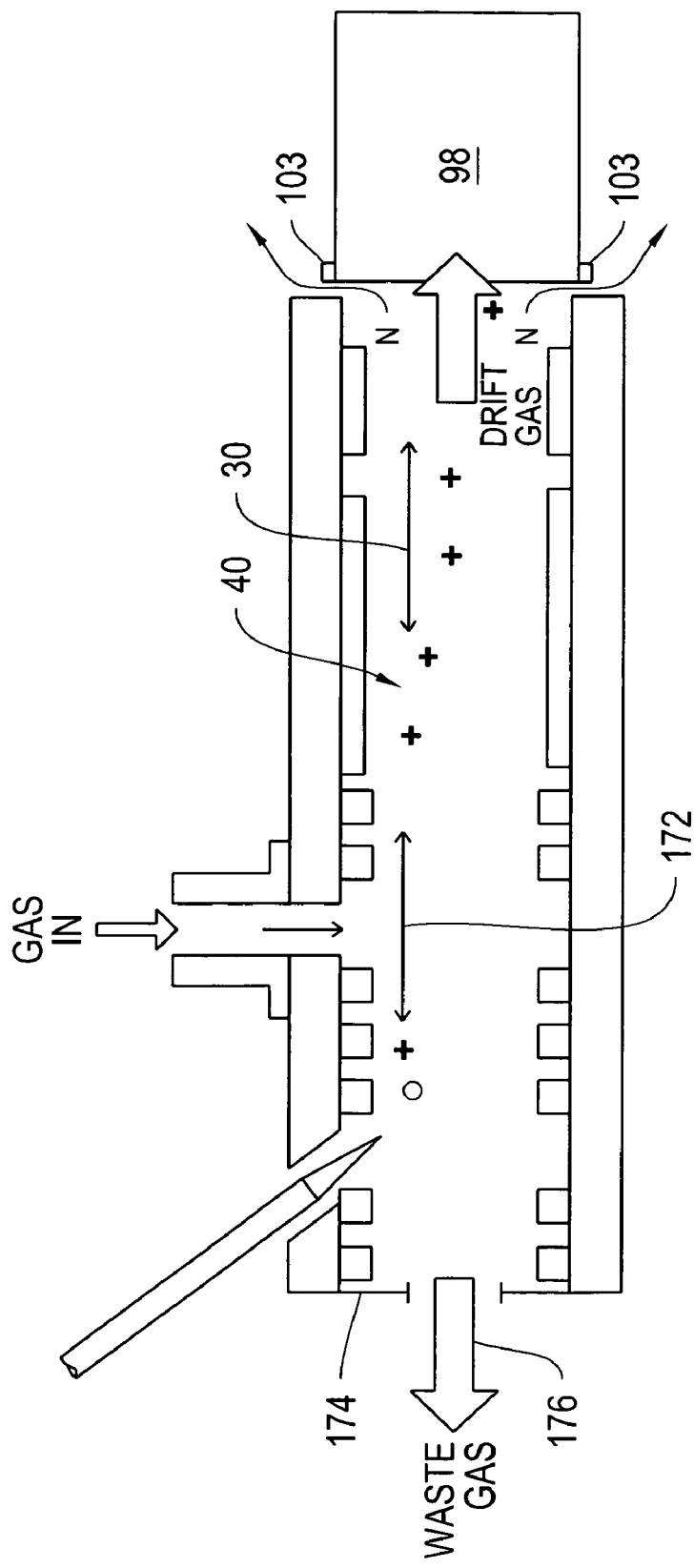

In the embodiment of FIG. 15B, mass spectrometer 98 is directly coupled to the end of the drift tube 30. An advantage of this design is that the ion filter 40 is kept free of sample neutrals by virtue of the split gas flow. This prevents clustering of neutral sample molecules with ions, and this results in higher detection accuracy. A venting device 103 for venting of neutrals N keeps neutrals out of the MS intake.

A baffle 174 may be placed as shown to regulate the velocity of waste gas flow stream 176 relative to the velocity of drift gas flow stream 172. Typically, drift gas flow stream 172 is at a higher velocity than waste gas flow stream 176. Other means for creating a waste gas flow stream of a velocity different than the drift gas flow stream, however, are within the scope of this invention.

In the embodiments of FIG. 15A, 15B, various sample preparation sections can be used, whether simple a port to draw in ambient air samples, or electrospray, gas chromatograph, liquid chromatograph, or the like. Regardless of what is used, the split gas embodiment shown can prevent clustering and allows better identification of ion species.

Generally the sample ions tend to be found in monomer or cluster states. The relationship between the amount of monomer and cluster ions for a given ion species is dependent of the concentration of sample and the particular experimental conditions (e.g., moisture, temperature, flow rate, intensity of RF-electric field). Both the monomer and cluster states provide useful information for chemical identification. It will be useful to investigate the same sample separately in a condition which promotes clustering, and in an environment that promotes the formation of only the monomer ions. A planar two channel planar DMS of an embodiment such as shown in FIG. 16 can be used to achieve this.

Figure 16:
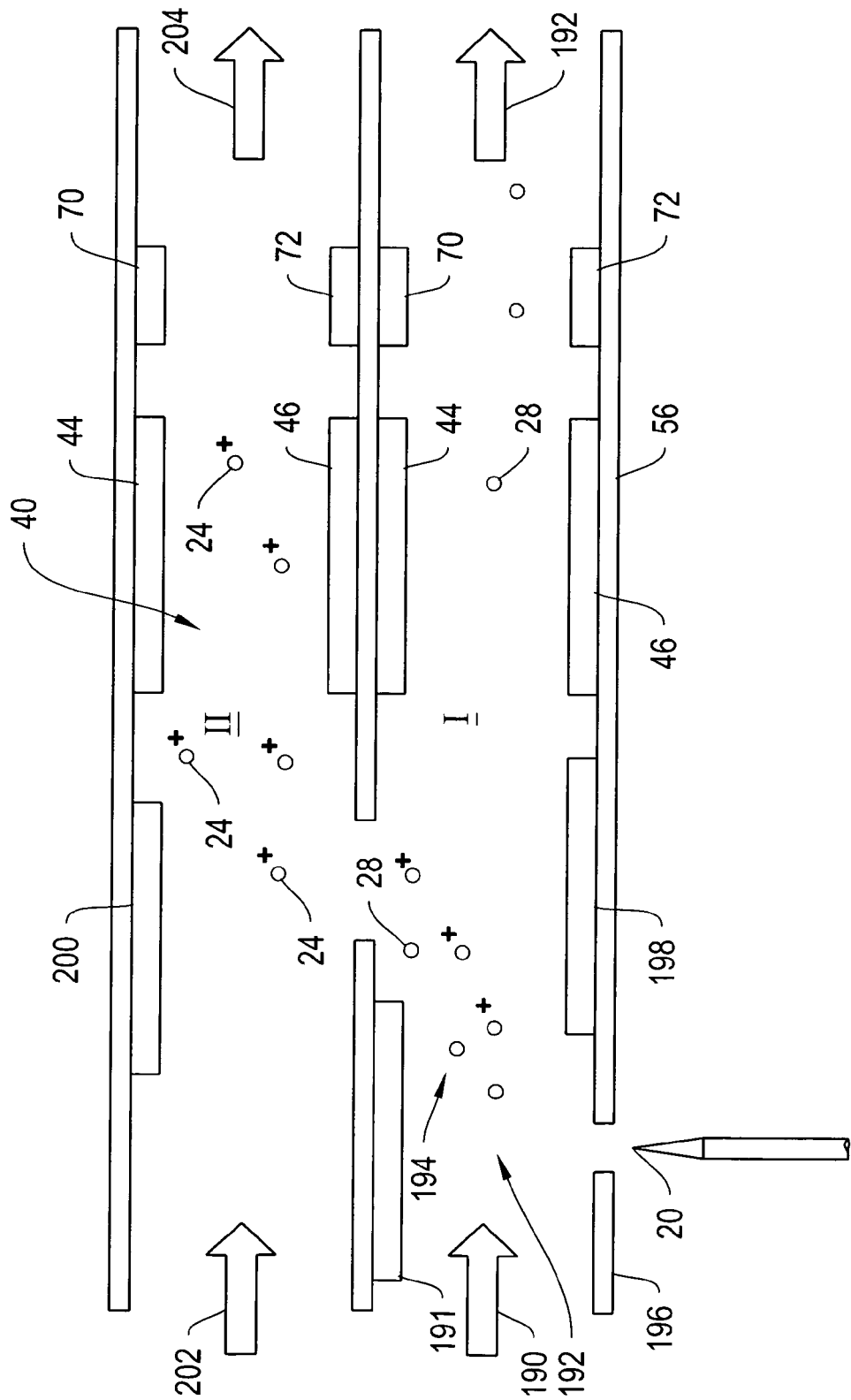
FIG. 16 shows a dual channel embodiment according to an illustrative embodiment of the invention.

In the dual channel embodiment of FIG. 16, a first channel "I" is shown for receipt of ions 24, and molecules 28 in a drift gas flow 190 in ion region 194. Also included are planar DMS filter electrodes 44, 46 and detector electrodes 70, 72.

To interrogate the sample ions in the monomer state, the ions are extracted from the flow stream (by action of an electric field between electrodes 198 and 200) and they flow up into upper chamber "II". The neutral molecules 28, typically solvent, continue to flow through channel "I" and exit at drift gas exhaust 192. The potential difference between the electrospray tip 20 and the attraction electrode 191 accelerates the ions into the ion region 194 through orifice 196 in substrate 56. A second gas flow 202 prevents the sample neutrals from entering chamber "II" and carries ions 24 to planar DMS filter 40 (electrodes 44, 46 in Chamber II), and the passed ions are then detected, such as with detector electrodes 70, 72 as in FIG. 2 or with a mass spectrometer as in FIG. 3A. The second gas flow 202 exhausts as flow 204. When the deflection and attractor electrodes 198, 200 are not energized, then the sample ions can be observed in the cluster state in chamber "I" by the local detector electrodes 72 and 70. By alternatively energizing and not energizing electrodes 198 and 200 significantly more information can be obtained to better identify the chemical sample.

Figure 17:
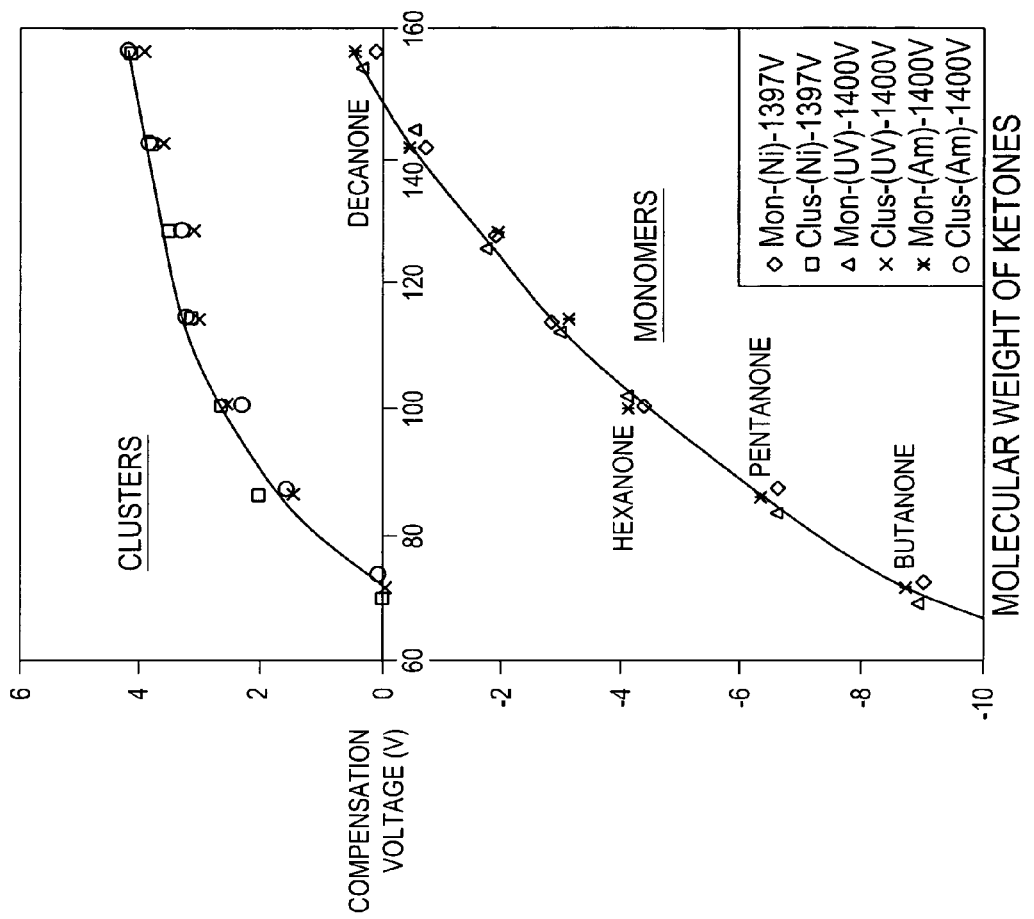
FIG. 17 shows dependence of Ketones on compensation voltage for different ionization sources according to an illustrative embodiment of the invention.
Figure 18:
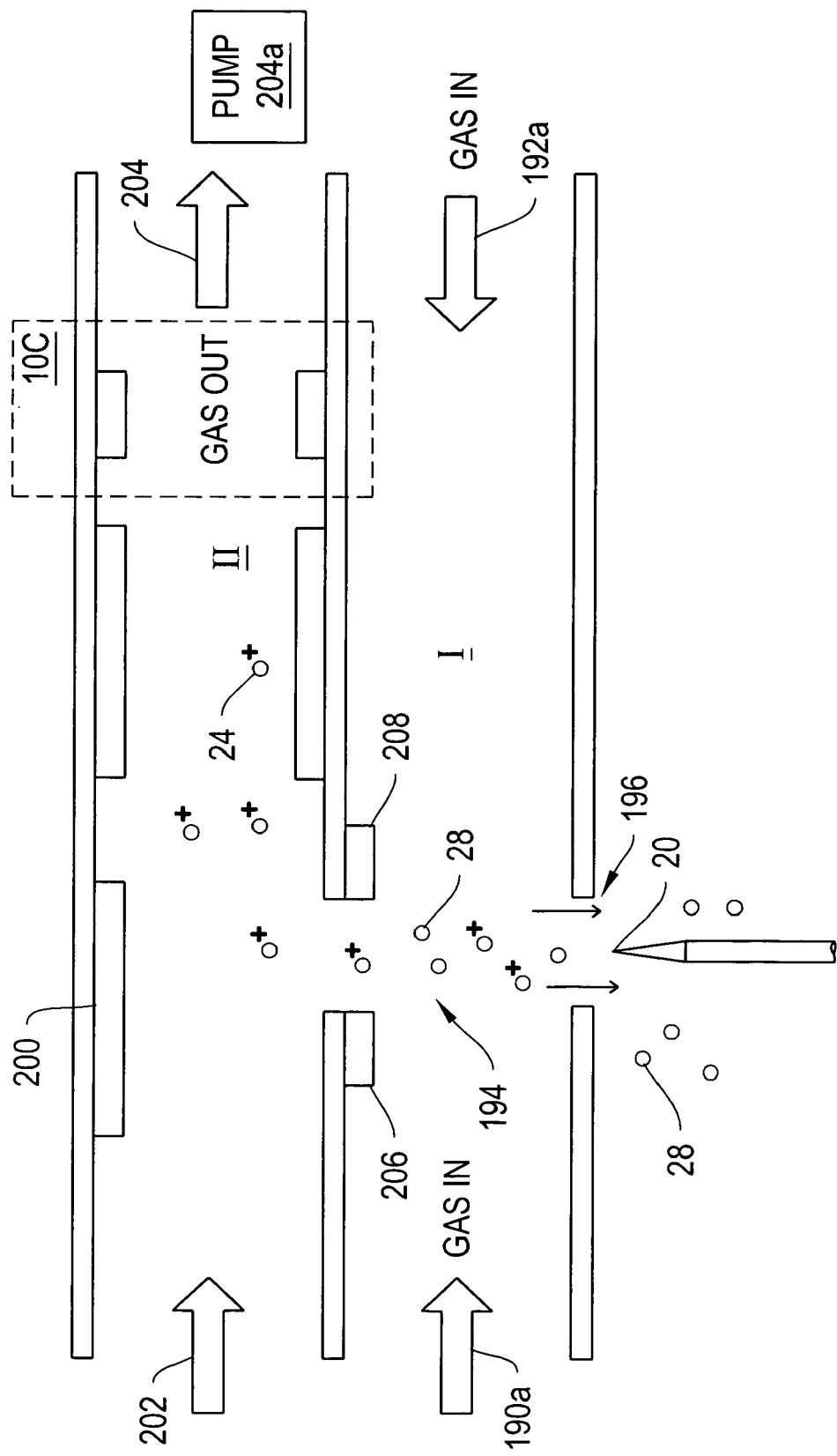
FIG. 18 shows a dual channels according to an illustrative embodiment of the invention.

FIG. 17 shows a homologous series of Ketone samples obtained in one practice of the invention, ranging from Butanone to Decanone. From the figure it is evident that for the same chemical species the cluster ions (top plot) require very different compensation signals compared to the monomer ions (bottom plot). So by observing the difference in peak position of the monomer and cluster peak the level of identification of the chemical compound can be significantly increased. For example, for Butanone the peak position in the monomer state occurs close to −9 volts while the cluster peak is around zero. For Decanone for example, the monomer peak is close to zero while the cluster peak is at around +4 volts. The motivation for the embodiment shown in FIG. 18 is the same as that of embodiment 16. In this system switching between a monomer state and cluster state operating condition is achieved by control of a curtain gas flow 190a and 192a. With the curtain gas applied, sample neutrals 28 are prevented from entering channel "II" and ions in the monomer state can be investigated. Curtain gases 190a and 192a may flow in the same direction and exhaust at orifice 196 for example. Meanwhile the gas flows in channel "II" remain in the same configuration as the system in FIG. 16 Guiding electrodes 206 and 208 are included to guide the ions into channel "II". Attraction electrode 200 is also used to attract ions into channel "II". When the curtain gas is turned off, ions in the cluster state may be observed since sample neutrals and sample ions may now be drawn into channel "II" using a pump 204a. Gas flows 202 and 204 may also be used. The output section may be connected to a mass spectrometer.

In application of the present invention, the high field asymmetric ion mobility filtering technique uses high frequency high voltage waveforms. The fields are applied perpendicular to ion transport, favoring a planar configuration. This preferred planar configuration allows drift tubes to be fabricated inexpensively with small dimensions, preferably by micromachining. Also, electronics can be miniaturized, and total estimated power can be as low as 4 Watts (unheated) or lower, a level that is suitable for field instrumentation.

We have described novel apparatus that combines electrospray and filtering components. We further disclose micromachined planar DMS-electrospray interface chips. The planar DMS-electrospray interface chips offer unique benefits compared to all prior bio-molecule-filtering methods for electrospray mass spectrometry. At the same time this approach can be used in conjunction with many in-liquid separation techniques such as capillary electrophoresis.

Figure 19:
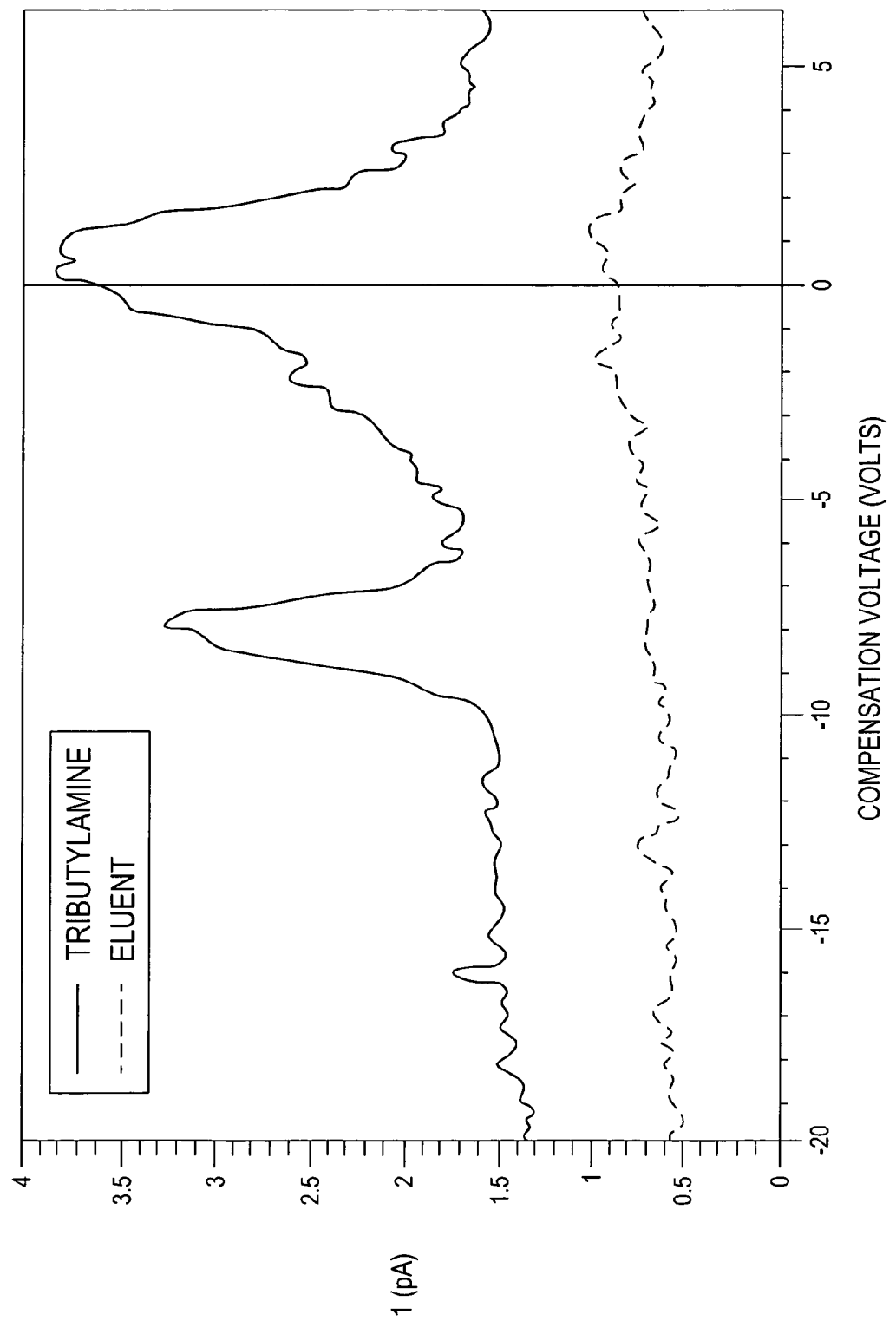
FIG. 19 shows detection spectra according to an illustrative embodiment of the invention.

In practice of an embodiment of the invention, tributylamine was electrosprayed into the planar DMS filter and detector. Resulting spectra are shown in FIG. 19 for the amine in solvent and for the solvent eluent alone. There is virtually no response for the eluent alone, and significant response to the amine. This demonstrates practical value and function of the invention.

The present invention provides improved chemical analysis in a compact and low cost package. The present invention overcomes cost, size or performance limitations of prior art TOF-IMS and DMS devices, in novel method and apparatus for chemical species discrimination based on ion mobility in a compact, fieldable package. As a result a novel planar, high field asymmetric ion mobility spectrometer device can be intimately coupled with a electrospray tip to achieve a new class of chemical sensor, i.e., either as a standalone device or coupled to an MS. A fieldable, integrated, planar DMS chemical sensor can be provided that can rapidly produce accurate, real-time or near real-time, in-situ, orthogonal data for identification of a wide range of chemical compounds. These sensors have the further ability to render simultaneous detection of a broad range of species, and have the capability of simultaneous detection of both positive and negative ions in a sample. Still further surprising is that this can be achieved in a cost-effective, compact, volume-manufacturable package that can operate in the field with low power requirements and yet it is able to generate orthogonal data that can fully identify various a detected species.

Another advantage of the planar DMS design over prior art cylindrical designs is the ability of the planar DMS to filter and act on all types of ions with different alpha α dependencies on electric field strength (see background section for more detail on alpha α). This fact allows significant reduction in the complexity of performing measurements in unknown complex sample mixtures.

It will be appreciated by a person skilled in the art that in the prior art cylindrical design shown in FIG. 12C-D, the radial electric field distribution is non-uniform. Meanwhile, in practice of the present invention, such as the planar DMS shown in FIG. 2,B, the field distribution between the ion filter electrodes (neglecting fringing fields) in the planar DMS design is uniform and the field is uniform.

It has been found that the time for separation of ions in the planar DMS design is significantly less (~10 times) than in the prior art cylindrical DMS (FAIMS) design when reaching conditions for ion focusing.

Figure 20:
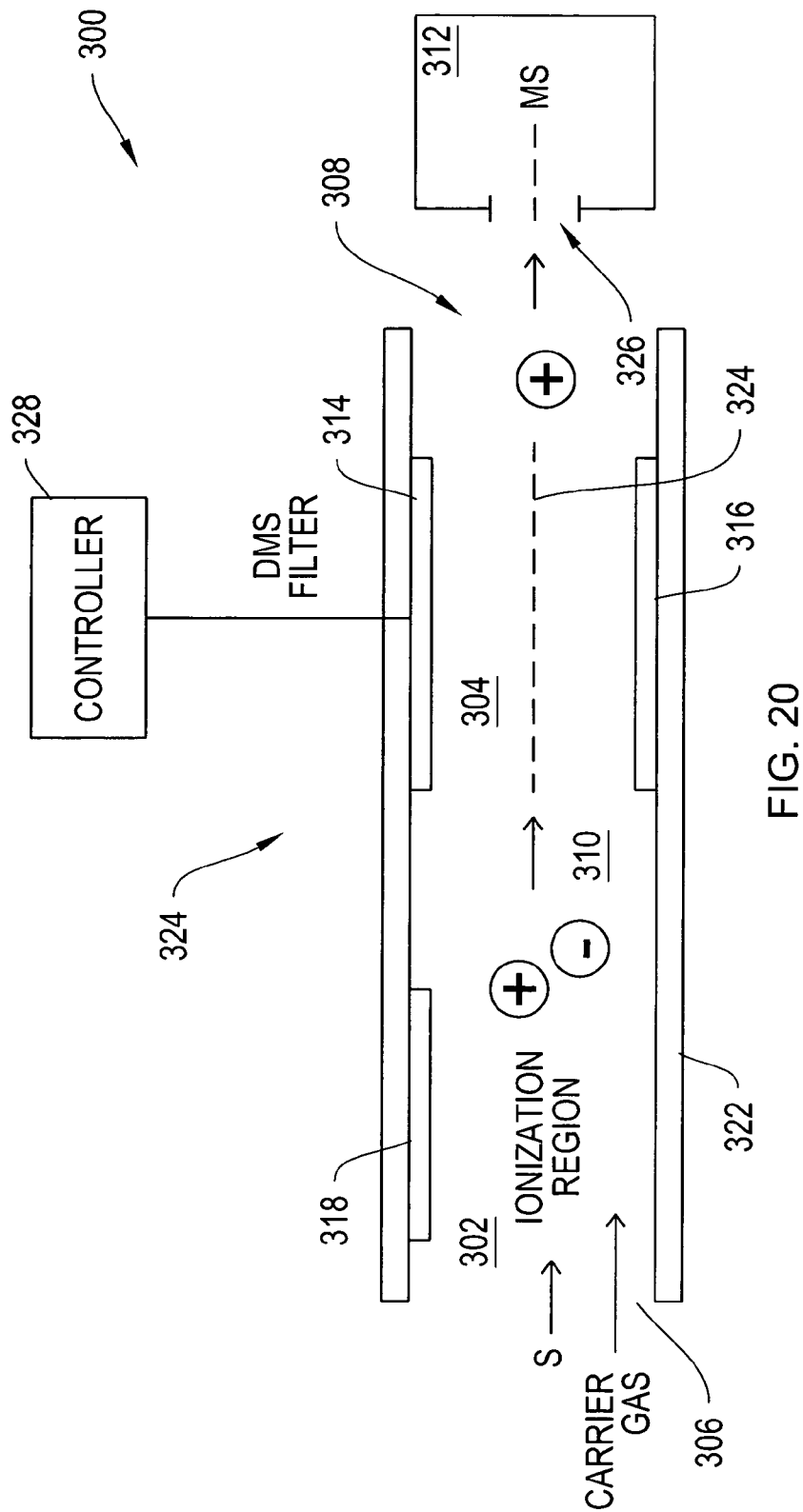
FIG. 20 is a diagram of an in-line DMS-MS analyzer according to an illustrative embodiment of the invention.

FIG. 20 is a diagram of an in-line DMS-MS analyzer 300 according to an illustrative embodiment of the invention. The analyzer 300 includes an ionization region 302, and analyzer region 304, a pre-filter inlet 306, pre-filter outlet 308, a flow path 310, and MS 312. The analyzer region 304 may include a DMS filter electrodes 314 and 316 between which an asymmetric field is formed to pass through select ions to the MS 312. The ionization region 302 may include an ionization source 318 which may be a radioactive source, capacitive discharge source, ESI, nano-ESI, MALDI, LC output tip, or other like ionization source. In one embodiment, at least the portion of the flow path 310 through the analyzer region 304 is substantially in-line or along the same longitudinal axis 324 as the entrance or inlet 326 of the MS 312. In another embodiment, the pre-filter outlet 308 is offset from the inlet 326 to the MS 312 to enable the expulsion of neutrals from the analyzer 300 instead of allowing neutrals to enter the MS 312 along with filtered ions. In one embodiment, the DMS filter electrodes 314 and 316 are micromachined and/or formed onto, or attached to, insulating substrates 320 and 322 respectively. In certain embodiments, the pre-filter assembly 324, which at least includes the analyzer region 304, includes an integrated chip assembly for housing the analyzer region 304.

In operation, a sample S is flowed along the flow path 310 from the pre-filter inlet 306 to the ionization region 302 where the sample S is ionized. The ions then flow through the analyzer region 304 where upon select ions are allowed to pass by on the condition of the electric field between the electrodes 314 and 316. The condition may include a compensation voltage setting. The select ions that are filtered or allowed to pass through the analyzer region 304 are then delivered to the MS 312. In one embodiment, the electric fields in the analyzer region 304 are removed and/or turned off to allow substantially all of the ions to flow into the MS 312. One advantage of the in-line configuration of analyzer 300 is that a carrier gas can continuously flow sample ions through the pre-filter 324 regardless of whether ions are being filtered in the analyzer region 304. Thus, in certain embodiments, ion mobility filtering is turned on or off which does not effect the ability to flow ions into the MS 312. Thus, it is not necessary to change to flow path 310 or remove the pre-filter 324 when the analyzer 300 is used without the need of the pre-filter 324 and/or DMS filtering.

In certain embodiments, the analyzer 300 includes a controller 328 that may perform the same function as, for example, controller 10D of FIG. 1. In one embodiment, the controller 328 is capable of activating or de-activating the filter electrodes 314 and 316 so as to turn on or turn off the filter voltage applied to the electrodes 314 and 316 and, thereby, enable the generation or removal of any filter fields associated with the filter electrodes 314 and 316.

Figure 21:
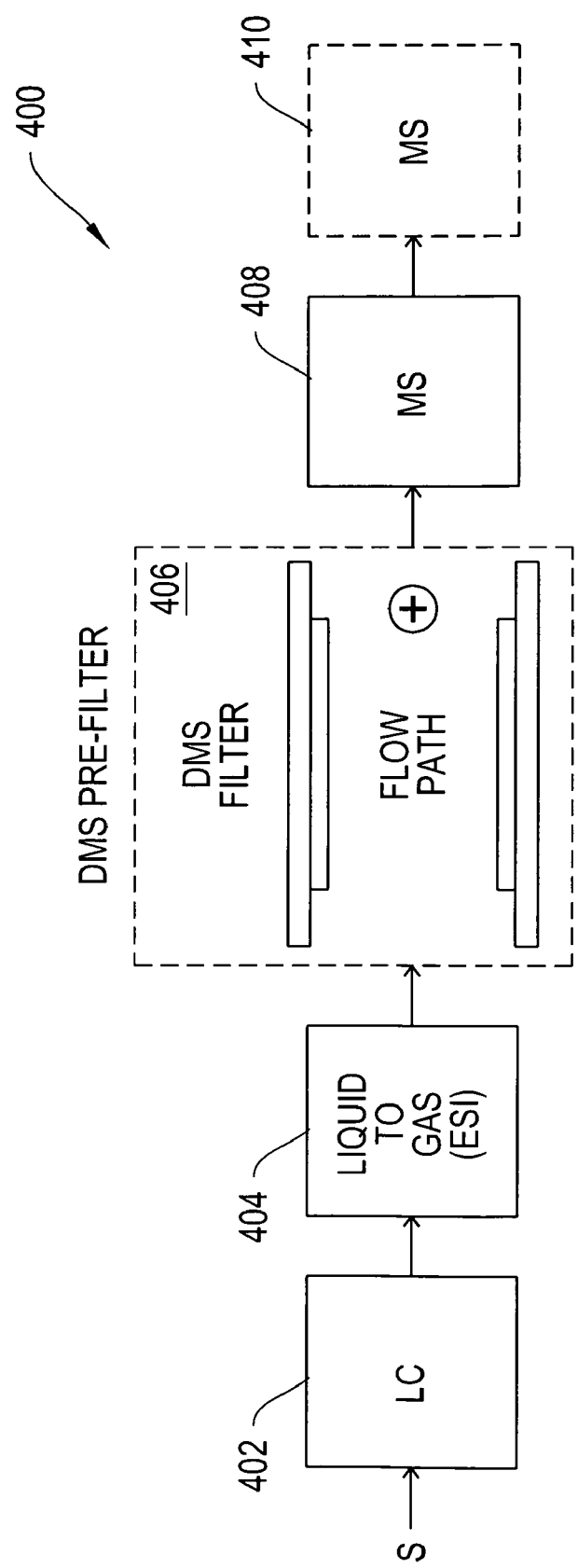
FIG. 21 is a block diagram of a LC-ES-DMS-MS analyzer according to an illustrative embodiment of the invention.

FIG. 21 is a block diagram of a LC-DMS-MS analyzer 400 according to an illustrative embodiment of the invention. The analyzer 400 includes an LC 402, an ESI 404, a DMS pre-filter 406, an MS 408, and, optionally, a second MS 410. In operation, the LC 402 receives a liquid sample and performs a separation of the sample via a column. The LC 402 may include a liquid-to-gas conversion section or interface with an ESI 404 to convert the liquid sample S into a gas and/or vapor before entry into the DMS pre-filter 406. The pre-filter 406 may include a DMS or other ion mobility based analyzer or combination of multiple ion mobility based analyzers to filter select ion species through to the MS 408. In an optional configuration, a second MS 410 or more may be employed for further detection and/or analysis.

In certain embodiments, the pre-filter 406 is detachable, modular, and/or replaceable. In one embodiment, the pre-filter 406 is a disposable single use or limited use component. In another embodiment, the pre-filter 406 is detachable to enable the interchange of the same type of pre-filter or another type of pre-filter with one or more ion mobility filters arranged in series, parallel, or a series-parallel combination. In one embodiment, the pre-filter 406 is included in a detachable integrated chip assembly that is mountable onto a receptor for the MS 408. In another embodiment, the pre-filter 406 is permanently or semi-permanently mounted to a receptor.

In certain embodiments, the pre-filter assembly includes one or more carrier gas inlets, one or more dopant inlets, one or more diverter gas inlets, and/or one or more curtain gas inlets or outlets. The analyzer 400 may be advantageously employed in the fields of Drug Metabolism and Pharmacokinetics (DMPK), proteomics, biomarkers, genomics, cytomics, bioinformatics, metabolomics, lipidomics, systems biology, transcriptomics, and other like fields.

Figure 22:
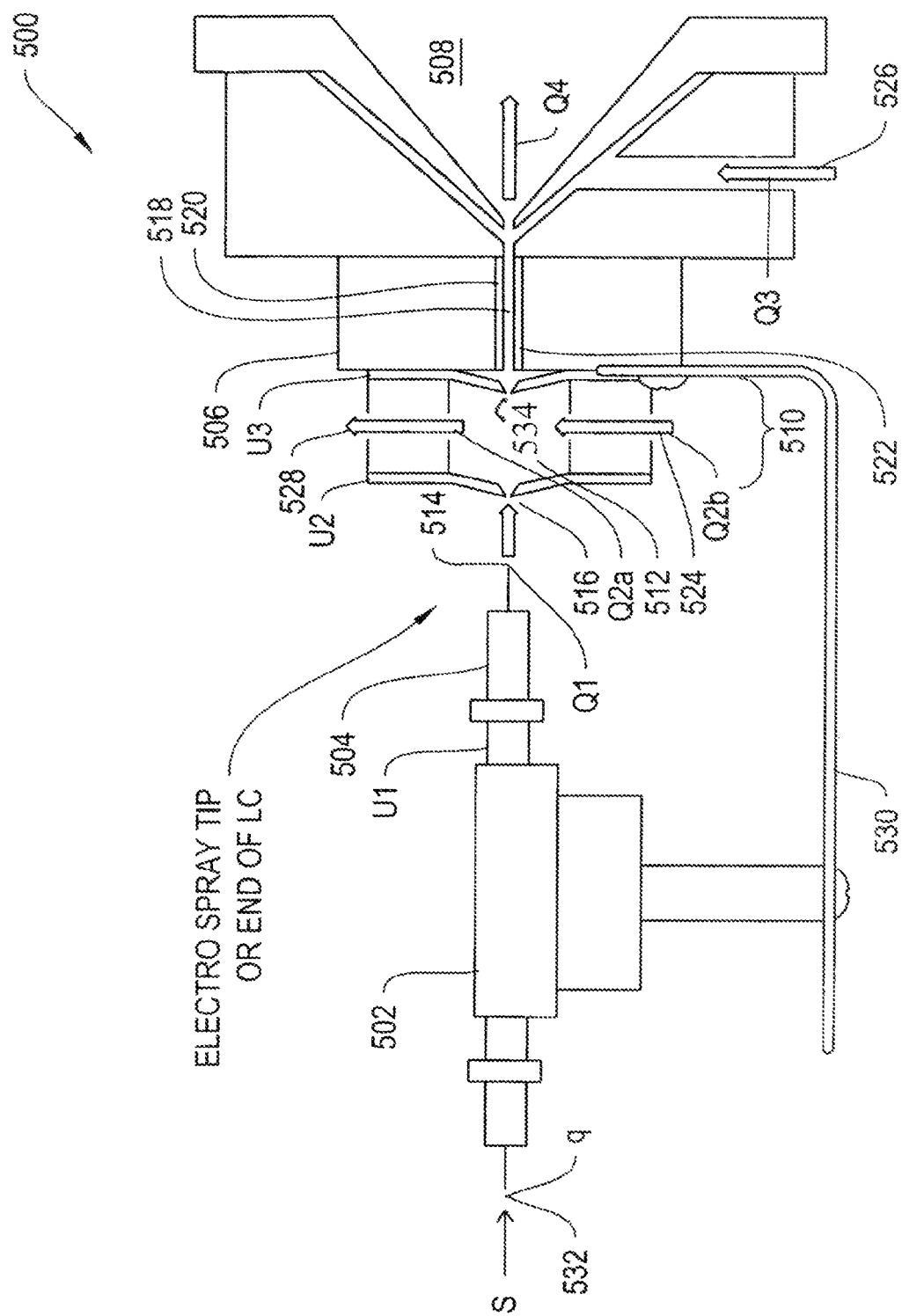
FIG. 22 is a schematic diagram of a LC-DMS-MS analyzer according to an illustrative embodiment of the invention.

FIG. 22 is a schematic diagram of a LC-DMS-MS analyzer 500 according to an illustrative embodiment of the invention. The analyzer 500 includes sample S inlet 532, LC 502, liquid-to-gas conversion unit 504, tip 514, pre-filter assembly 510, DMS pre-filter 506, chamber 512, gas inlets 524 and 526, gas outlet 528, chamber sample inlet 516, support bracket 530, and MS 508. The DMS pre-filter 506 includes filter electrodes 518 and 520.

In operation, a liquid sample S is introduced at inlet 532 into the LC 502 which separates components of the sample S using a column. The unit 504 and tip 514 convert the liquid to gas for introduction to the inlet 516 and gas chamber 512. The tip 514 may be the tip of an electrospray ionization source. A carrier gas including one or more dopants may be introduced into the chamber 512 via inlet 524. Also, the chamber 512 may be maintained at a low pressure than the atmosphere in proximity of the tip 514 to encourage flow of sample ions into the chamber 512. The outlet 528 may be employed to exhaust excess gas and/or regulate pressure in the chamber 512. In certain embodiments, the pressure in the chamber 512 may be relatively higher than the atmosphere in proximity to the tip 514 to enable a counterflow of gas (counter to the flow of sample S ions) for desolvating and/or preventing neutral interferent particles from entering the pre-filter 510. Sample ions are introduced into the DMS filter 506 via inlet 534. Select ions may be filtered by adjusting the RF and/or DC compensation voltage applied to electrodes 520 and 522. Although not shown, a spacer may be employed along a portion or up to the full length of the analyzer region 518 to space apart the electrodes 520 and 522. Upon exiting the analyzer region 518, the select ions are transported into the MS 508. The outlet from the analyzer region 518 may be offset from the MS 508 inlet to reduce the introduction of neutrals and/or other interferents into the MS 508.

The analyzer 500 may includes the following setting ranges to enable sample analysis operations which includes about: U1=2000-4000 v, U1=500-800 v, U3=100-300 v, U4=100-300 v, U5=10-100 v, q=10-300 uL/min, Q1=0.1-1.1 L/min, Q2b=0.1-0.4 L/min, Q3=0.2-0.5 L/min, and Q4=0.8-1.5 L/min. Q2a setting may vary.

In various embodiments, the size and power consumption of a DMS-MS analyzer system are reduced by orienting the MS in relation to the DMS in such a way as to enable a significantly lower ion flow rate into the MS. Thus, a significantly smaller vacuum pump or pumps are required to maintain the proper vacuum in the MS which, thereby, reduces the DMS-MS analyzer size and power requirements.

Figure 23:
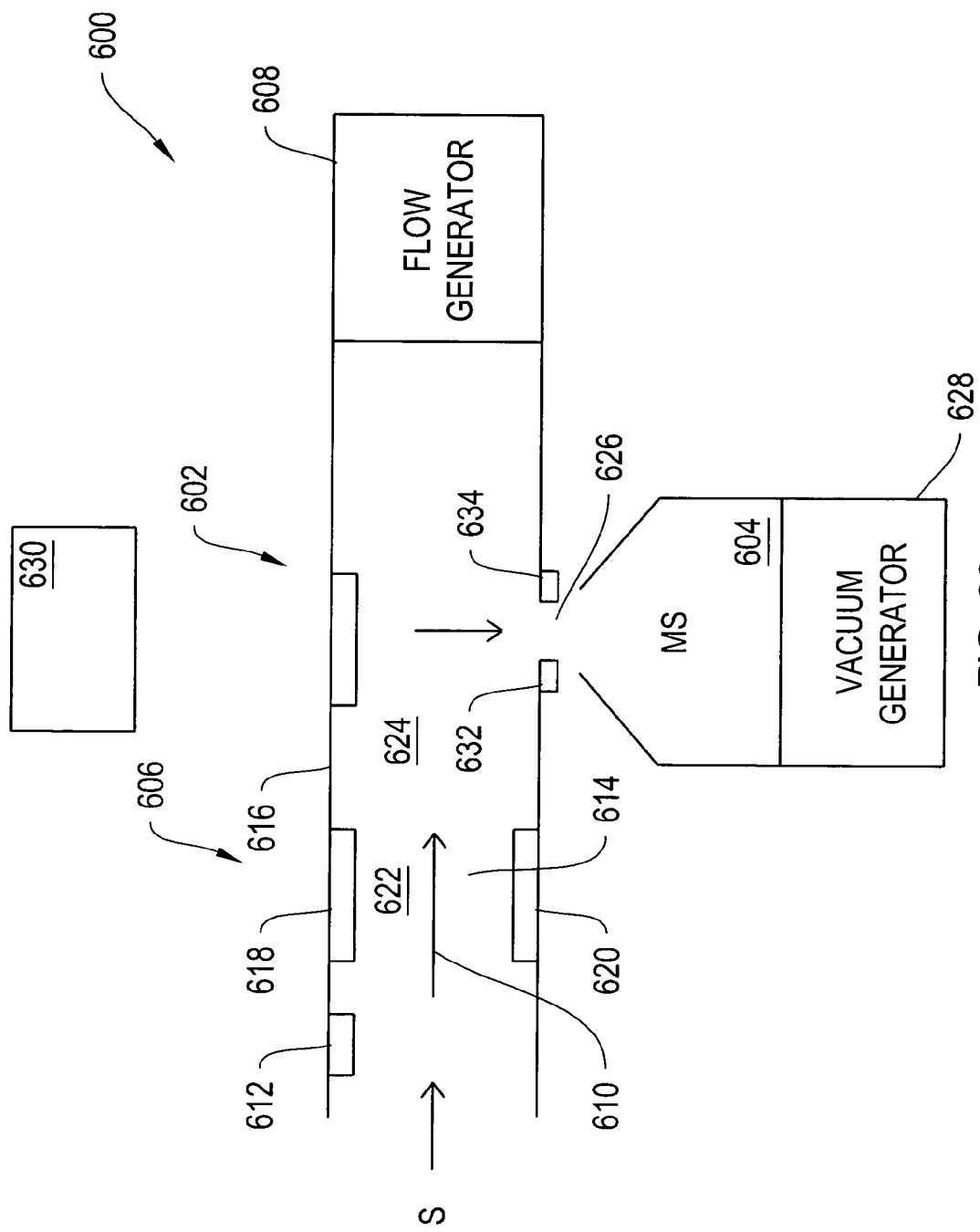
FIG. 23 is diagram of the DMS-MS analyzer including a diverter assembly that enables a reduced flow rate into the MS according to an illustrative embodiment of the invention.

FIG. 23 is diagram of an ion analyzer 600 including a diverter assembly 602 that enables a reduced flow rate of ions into an MS 604 from a DMS 606 according to an illustrative embodiment of the invention. In one embodiment, the ion analyzer 600 includes a flow generator 608 that generates a flow of ions 610 from an ion source 612 at a first flow rate. The ion analyzer 600 may be included in a chip assembly (see FIG. 24) that is coupled to receive the flow of ions 610 from the ion source 612.

The DMS 606 of the analyzer 600 may include a spaced DMS filter 614 including a first substrate 616 with a first filter electrode 618 connected to the substrate 616. A second filter electrode 620 may be spaced away from the first filter electrode 618 to thereby define an analytical gap 622 between the first and second filter electrodes 618 and 620 and a portion of a flow path 624 through which the ion flow occurs.

In one embodiment, the ion analyzer 600 includes a mass spectrometer 604 that receives a portion of the ions from the flow path 624. The mass spectrometer 604 includes an inlet 626 which is offset from the flow of ions 610 in the flow path 624. Thus, the inlet 626 is offset because the inlet is not positioned substantially in the direction of the ion flow 610. In one embodiment, the ion analyzer 600 includes a diverter assembly that redirects the flow of at least a portion of the ions of the ion flow 610 toward the inlet 626 of the MS 604. However, the portion of ions from the first flow path are flowed through the inlet 626 at a second flow rate that is less than the flow rate of the ion flow through the DMS filter 606. By reducing the flow rate into the MS 604 substantially, the vacuum generator 628 is requires less power and capacity to maintain the required vacuum pressure to enable ion analysis in the MS 604.

Therefore, the size of the vacuum generator, and amount of power used by it, can be greatly reduced, resulting in a more compact and portable ion analyzer 600. In certain embodiments, the vacuum generator includes a two-stage vacuum pump system including a first rough pump and a second cryogenic pump. In certain embodiments, one or more vacuum pumps are micromachined. The vacuum generator 628 may maintain a vacuum of greater than about $10^{-1}$, $10^{-2}$, $10^{-3}$, $10^{-4}$, $10^{-5}$, and $10^{-6}$ Torr. In certain embodiments, the flow rate of the ion flow 610 through DMS 606 may be greater than about 100 cc/min, 200 cc/min, 300 cc/min, 400 cc/min, and 500 cc/min.

In one embodiment, a controller 630 is connected to at least one of the first and second filter electrodes 618 and 620 to generate a time varying electric field between the first and second filter electrodes 618 and 620 with a field characteristic for separating ion species while various ion species are flowing through the analytical gap 622. The vacuum generator 628 may maintain a selected vacuum within the mass spectrometer 604 in response to the ion flow rate at the inlet 626 of the mass spectrometer 604.

In one embodiment, the diverter assembly includes a diverter electrode 602 that directs ions toward the inlet 626 of the first mass spectrometer 604. In another embodiment, the diverter assembly includes one or more attraction electrodes 632 and 634 that attract ions toward the inlet 626.

Figure 24:
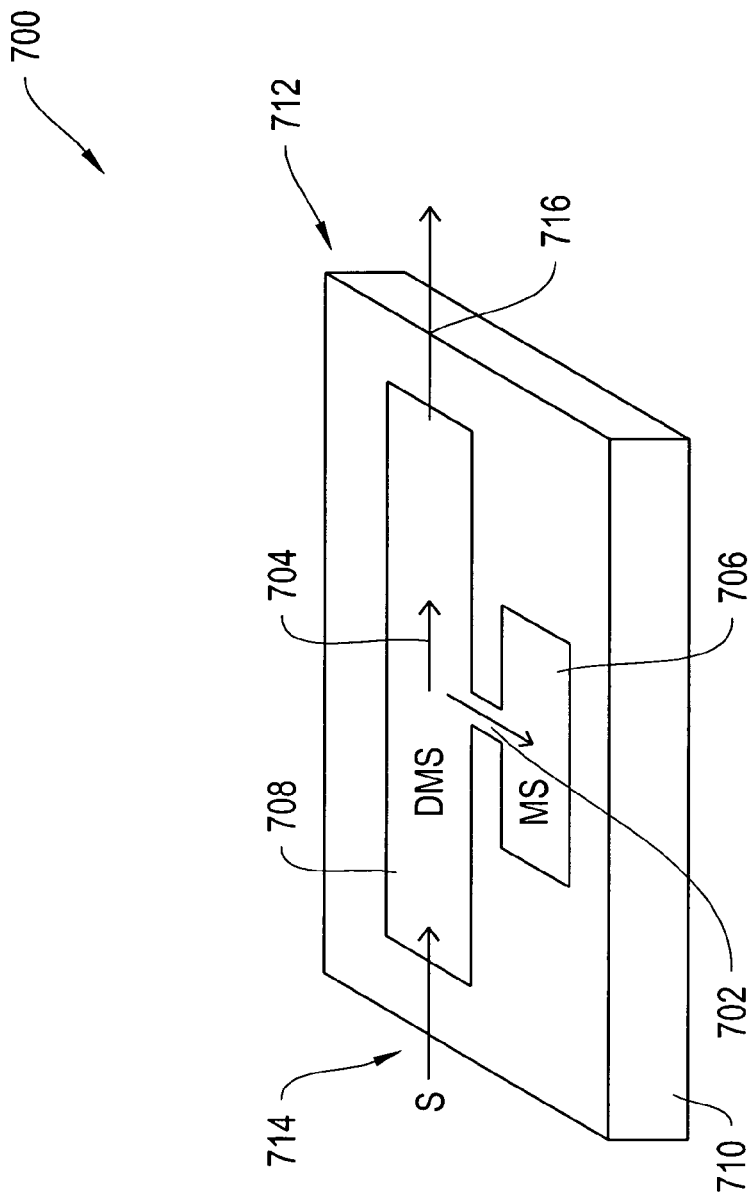
FIG. 24 is a diagram of a integrated DMS-MS analyzer where the MS inlet is offset from the flow of the DMS according to an illustrative embodiment of the invention.

FIG. 24 is a diagram of a integrated DMS-MS analyzer 700 where the MS 706 inlet 702 is offset from the ion flow 704 of the DMS 708 according to an illustrative embodiment of the invention. In one embodiment, the DMS-MS analyzer 700 is included on one or more substrates 710 of an integrated chip assembly 712. The chip assembly may include a sample inlet 714 and exhaust 716. Although not shown in FIG. 24, the chip assembly 712 may interface with various electronics such as the controller 630 of FIG. 23. The chip assembly 712 may also be coupled to one or more flow generators and/or vacuum generators to support ion flow in the DMS 708 and a vacuum in the MS 706. In certain embodiments, the integrated MS 706 may include an integrated and/or micromachined MS, such as the Ionchip® by Microsaic® Systems of Woking, Surry, of the United Kingdom. The integrated MS 706 may include an integrated MS of the type described in U.S. Pat. Nos. 5,536,939, 6,972,406, and 7,208,729, the entire contents of which are incorporated herein by reference.

Figure 25:
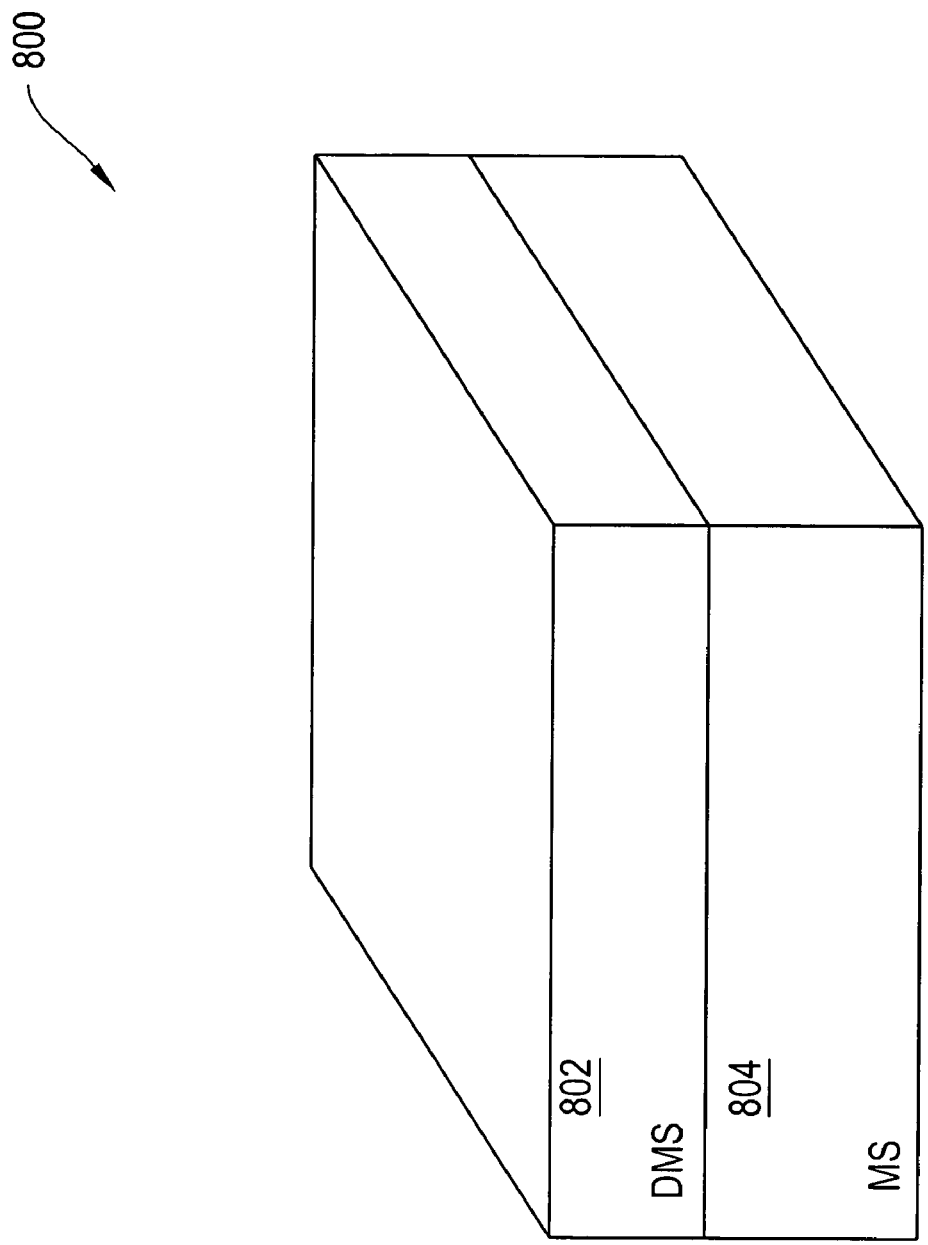
FIG. 25 is a diagram of an integrated multilayered DMS-MS analyzer according to an illustrative embodiment of the invention.

FIG. 25 is a diagram of an integrated multilayered DMS-MS analyzer 800 according to an illustrative embodiment of the invention. In certain embodiments, the analyzer 800 includes a DMS layer 802 including a DMS analyzer such as DMS 606 of FIG. 23 and a MS layer 804 including a MS such as MS 604 of FIG. 23.

Embodiments of the present invention may be practiced in method and apparatus using cylindrical, planar and other configurations and still remain within the spirit and scope of the present invention. Examples of applications for this invention include use in biological and chemical sensors, and the like. Various modifications of the specific embodiments set forth above are also within the spirit and scope of the invention. The examples disclosed herein are shown by way of illustration and not by way of limitation. The scope of these and other embodiments is limited only as set forth in the following claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for analyzing one or more ion species of a sample comprising, an ion source, a pre-filter assembly operating substantially at atmospheric pressure, including:

a planar differential mobility spectrometer filter having a filter inlet, the planar differential mobility spectrometer filter passing one or more ion species of the sample through a time-varying field applied by a waveform generator in an analytical gap between a pair of filter electrodes, including a first filter electrode and a second filter electrode, an outlet for providing a flow of ions from the differential mobility spectrometer filter, and a first mass spectrometer for receiving at an inlet at least a portion of the flow of ions from the pre-filter assembly and analyzing one or more ion species, and a controller for activating the planar differential mobility spectrometer filter when pre-filtering is desired and deactivating the planar differential mobility spectrometer filter when pre-filtering is not desired, wherein the filter inlet is positioned substantially in-line with the inlet of the first mass spectrometer.

2. The system of claim 1, wherein the filter inlet is in-line with the inlet of the first mass spectrometer when the longitudinal axis of the filter inlet and the analytical gap between the pair of filter electrodes is aligned with the longitudinal axis of the inlet of the first mass spectrometer.

3. The system of claim 2, wherein the time-varying field is adjustable and includes an adjustable compensation field.

4. The system of claim 3, wherein the controller includes a microprocessor.

5. The system of claim 2, wherein the ion source includes an electrospray ion source.

6. The system of claim 5 comprising a liquid chromatograph (LC) for delivering a liquid sample to the electrospray ion source.

7. The system of claim 6, wherein analyzing includes detection one or more ion species.

8. The system of claim 7, wherein the planar differential mobility spectrometer filter includes insulating substrates, at least one insulting substrate in communication with a filter electrode.

9. The system of claim 8, wherein the planar differential mobility spectrometer filter is included in a chip assembly.

10. The system of claim 6 comprising a second mass spectrometer for receiving and detecting ions from the first mass spectrometer, wherein analyzing including focusing a portion of the ions received from the planar differential mobility spectrometer filter.

11. A method for analyzing one or more ion species of a sample comprising, ionizing a portion of the sample to form ions, flowing ions into a filter inlet and through an analytical gap between a pair of planar filter electrodes including a first filter electrode and a second filter electrode, the filter operating substantially at atmospheric pressure, receiving at an inlet of a first mass spectrometer at least a portion of the flowing ions and analyzing one or more ion species, activating a time-varying field in the analytical gap between the pair of planar filter electrodes to pass through the one or more ion species of the sample when pre-filtering of the first mass spectrometer is desired and deactivating the time-varying field in the analytical gap between the pair of planar filter electrodes when pre-filtering is not desired, and positioning the filter inlet and the analytical gap between the pair of planar filter electrodes substantially in-line with the inlet of the first mass spectrometer.

12. The method of claim 11, wherein positioning the filter inlet and the analytical gap in-line with the inlet of the first mass spectrometer includes aligning the longitudinal axis of the filter inlet and the analytical gap between the pair of planar filter electrodes with the longitudinal axis of the inlet of the first mass spectrometer.

13. The method of claim 12, wherein the time-varying field is adjustable and includes an adjustable compensation field.

14. The method of claim 13 comprising controlling the activating and deactivating using a microprocessor.

15. The method of claim 12 comprising using an electrospray ion source to ionize a portion of the sample.

16. The method of claim 15 comprising eluting a liquid sample from a liquid chromatograph (LC) and delivering the sample to the electrospray ion source.

17. The method of claim 16, wherein analyzing includes detecting one or more ion species.

18. The method of claim 17 comprising forming at least one filter electrode of the pair of planar filter electrodes on an insulting substrate.

19. The method of claim 18, wherein the insulating substrate is included in a chip assembly.

20. The method of claim 16 comprising receiving and detecting ions from the first mass spectrometer at a second mass spectrometer, wherein analyzing including focusing a portion of the ions from the inlet.

21. A system for analyzing one or more ion species of a sample comprising, an electrospray ion source, a pre-filter assembly operating substantially at atmospheric pressure, including:

a planar differential mobility spectrometer filter having a filter inlet, the planar differential mobility spectrometer filter passing one or more ion species of the sample through a time-varying field applied by a waveform generator in an analytical gap between a pair of filter electrodes, including a first filter electrode and a second filter electrode, an outlet for providing a flow of ions from the differential mobility spectrometer filter, and an attraction electrode separated from the pair of filter electrodes;

a first mass spectrometer for receiving at least a portion of the flow of ions from the pre-filter assembly and analyzing one or more ion species, and a controller for activating the planar differential mobility spectrometer filter when pre-filtering is desired and deactivating the planar differential mobility spectrometer filter when pre-filtering is not desired, wherein the controller is configured to independently control application of a potential to the attraction electrode relative to the pair of filter electrodes.

22. The system of claim 21, wherein the controller is configured to apply a first potential to the attraction electrode, and apply the first potential plus at least one offset potential to at least one of the pair of filter electrodes.

23. The system of claim 22, wherein the attraction electrode is positioned proximate to the outlet.

* * * * *